(12) United States Patent
Johansen et al.

(10) Patent No.: US 8,697,384 B2
(45) Date of Patent: Apr. 15, 2014

(54) YKL-40 AS A GENERAL MARKER FOR NON-SPECIFIC DISEASE

(75) Inventors: Julia Johansen, Frederiksberg (DK); Stig Bojesen, Copenhagen Ø (DK); Børge Grønne Nordestgaard, Gentofte (DK); Hans Jørgen Nielsen, Kongens Lyngby (DK); Ib Jarle Christensen, Hillerød (DK)

(73) Assignees: Herlev Hospital, Herlev (DK); Hvidovre Hospital, Hvidorve (DK); Rigshospitalet, Copenhagen (DK)

( * ) Notice: Subject to any disclaimer, the term of this patent is extended or adjusted under 35 U.S.C. 154(b) by 51 days.

(21) Appl. No.: 12/812,409

(22) PCT Filed: Jan. 22, 2009

(86) PCT No.: PCT/DK2009/050014
§ 371 (c)(1),
(2), (4) Date: Nov. 4, 2010

(87) PCT Pub. No.: WO2009/092381
PCT Pub. Date: Jul. 30, 2009

(65) Prior Publication Data
US 2011/0045518 A1    Feb. 24, 2011

(30) Foreign Application Priority Data

| | | | |
|---|---|---|---|
| Jan. 23, 2008 | (DK) | ................................. | 2008 00089 |
| Sep. 15, 2008 | (DK) | ................................. | 2008 01292 |
| Sep. 15, 2008 | (DK) | ................................. | 2008 01293 |
| Sep. 15, 2008 | (DK) | ................................. | 2008 01294 |

(51) Int. Cl.
C12Q 1/37    (2006.01)

(52) U.S. Cl.
USPC ......................................................... 435/23

(58) Field of Classification Search
USPC ......................................................... 435/23
See application file for complete search history.

(56) References Cited

U.S. PATENT DOCUMENTS

| | | | |
|---|---|---|---|
| 5,726,061 A | | 3/1998 | Robbins et al. |
| 5,811,535 A | | 9/1998 | Adamou et al. |
| 6,060,590 A | | 5/2000 | Bryant et al. |
| 2002/0031793 A1* | | 3/2002 | Price et al. .................... 435/7.23 |
| 2002/0090658 A1* | | 7/2002 | Price et al. .................... 435/7.23 |
| 2003/0215847 A1 | | 11/2003 | Kirkpatrick |
| 2005/0065325 A1* | | 3/2005 | Price et al. .................. 530/388.1 |
| 2005/0209181 A1 | | 9/2005 | Akil et al. |
| 2006/0210552 A1 | | 9/2006 | Demopulos et al. |
| 2007/0161022 A1 | | 7/2007 | Kim et al. |
| 2007/0269831 A1* | | 11/2007 | Spriggs et al. ................... 435/7.1 |
| 2008/0171319 A1 | | 7/2008 | Urdea et al. |
| 2011/0070601 A1* | | 3/2011 | Kastrup ........................... 435/19 |
| 2012/0040354 A1* | | 2/2012 | Johansen et al. .............. 435/6.12 |
| 2012/0040355 A1* | | 2/2012 | Johansen et al. .............. 435/6.12 |
| 2012/0070853 A1* | | 3/2012 | Johansen et al. .............. 435/7.92 |

FOREIGN PATENT DOCUMENTS

| | | |
|---|---|---|
| EP | 0 710 251 | 5/1996 |
| EP | 1804062 | 7/2007 |
| JP | 2005102601 | 1/2005 |
| WO | WO 95/01995 | 1/1995 |
| WO | WO 99/46390 | 9/1999 |
| WO | WO 00/19206 | 4/2000 |
| WO | WO 00/38786 | 7/2000 |
| WO | WO 00/62070 | 10/2000 |
| WO | WO 01/29081 | 4/2001 |
| WO | WO 02/085459 | 10/2002 |
| WO | WO 02/097125 | 12/2002 |
| WO | WO 03/009808 | 2/2003 |
| WO | WO 03/054166 | 7/2003 |
| WO | WO 03/073822 | 9/2003 |
| WO | WO 03/074654 | 9/2003 |
| WO | WO 03/087830 | 10/2003 |
| WO | WO 2004/053157 | 6/2004 |
| WO | WO 2005/039397 | 5/2005 |
| WO | WO 2005/039487 | 5/2005 |
| WO | WO 2005/081980 | 9/2005 |
| WO | WO 2005/116901 | 12/2005 |

(Continued)

OTHER PUBLICATIONS

Kucur M. et al. Serum YKL-40 Levels in Patients with Coronary Artery Disease. Coronary Artery Disease 18(5)391-6, Aug. 2007.*
Kucur M. et al. Serum YKL-40 Levels in Patients with CAD. Diagnostic Methods 18(5)391-396, Aug. 2007.*
Benvenuti S, et al; oncogenic activation of the RAS/FAF signaling pathway impairs the response of metastic colorectal caners to anti-epidermal growth factor receptor antibody therapies. Cancer Res, 67, pp. 2643-2648 (2007).
Bergmann OJ, et al; "High Serum Concentration of YKL-40 is Associated with Short Survival in Patient with Acute Myeloid Leukemia". Clin Cancer Res 11(24), pp. 8644-8652, Dec. 15, 2005.

(Continued)

*Primary Examiner* — Ralph Gitomer
(74) *Attorney, Agent, or Firm* — Clark & Elbing LLP; Kristina Bicker-Brady; Todd Armstrong

(57) ABSTRACT

The present invention relates to methods of diagnosing the presence of a non-specific disease or disorder in a subject, wherein a determined level of YKL-40 above a reference level indicates the presence of a non-specific disease or disorder. The subject may suffer from a variety of diseases or disorders. The reference level may be a reference level obtained from healthy individuals or it may be a previous measurement obtained from the same subject. The present invention furthermore relates to a method for classifying the severity of a non-specific disease or disorder in a subject, wherein a determined level of YKL-40 above or below one or more reference levels gives the severity of said non-specific disease or disorder. The present invention further relates to a kit and a device that may be used in the method of the present invention comprising means for measuring the level of YKL-40 in a sample; and means for comparing the measured level of YKL-40 with at least one reference level of YKL-40.

21 Claims, 11 Drawing Sheets

(56) References Cited

FOREIGN PATENT DOCUMENTS

| WO | WO 2006/009702 | 1/2006 |
|---|---|---|
| WO | WO 2006/050475 | 5/2006 |
| WO | WO 2006/054297 | 5/2006 |
| WO | WO 2006/062094 | 6/2006 |
| WO | WO 2006/089549 | 8/2006 |
| WO | WO 2006/133923 | 12/2006 |
| WO | WO 2007/027748 | 3/2007 |
| WO | WO 2007/035651 | 3/2007 |
| WO | WO 2007/056523 | 5/2007 |
| WO | WO 2007/067813 | 6/2007 |
| WO | WO 2007/076439 | 7/2007 |
| WO | WO 2007/082352 | 7/2007 |
| WO | WO 2007/093819 | 8/2007 |
| WO | WO 2007/123976 | 11/2007 |
| WO | WO 2007/147011 | 12/2007 |
| WO | WO 2008/008284 | 1/2008 |
| WO | WO 2008/031056 | 3/2008 |
| WO | WO 2008/048508 | 4/2008 |
| WO | WO 2008/068428 | 6/2008 |
| WO | WO 2008/077165 | 7/2008 |
| WO | WO 2008/080195 | 7/2008 |

OTHER PUBLICATIONS

Bigg HF, et al; "The mammalian chitinase-like lectin, YKL-40, binds specifically to type I collagen and medulates the rate of type I collagen fibril formation". J Biol Chem, 281, pp. 21082-21095 (2006).
Bojesen SE et al; "Integrin β3 leu33pro homozygosity and risk of cancer". J Natl Cancer Inst, 95 pp. 1150-1157 (2003).
Boot RG et al; "Strong induction of members of the chitinase family of proteins in atherosclerosis. Chitotriosidase and human cartilage gp-39 expressed in lesion macrophages". Arterioscler Thromb Vasc Biol, 19, pp. 687-694 (1999).
Cintin et al; "Postoperative elevation in serum YKL-40 in patients with colorectal cancer is related to short survival". Proceedings of the Annual Meeting of the American Association for Cancer Research, New York, NY, US. vol. 41, Abstract #4060, p. 639, Mar. 1, 2000.
De Ceuninck F. et al; "YKL-40 (Cartilage gp-39) induces proliferative events in cultured chondrocytes and synoviocytes and increases glycosaminoglycan synthesis in chondrocytes". Biochem Biophys Res Commun, 285, pp. 926-931 (2001).
Johansen JS et al; "Identification of proteins secreted by human osteoblastic cells in culture". J Bone Miner Res, 7, pp. 501-512 (1992).
Johansen JS et al; "Serum YKL-40, a new prognostic biomarker in cancer patients?" Cancer Epidemiol Biomarkers Prev, 15, pp. 194-202 (2006).
Kushner I. et al; "What does minor elevation of C-reactive protein signify?" Am J Med, 119, pp. 166.e17-166.e28 (2006).
Ling H. et al; "The chitinase 3-like protein human cartilage glycoprotein 39 inhibits cellular responses to the inflammatory cytokines interleukin-1 and tumour necrosis factor-alpha". Biochem J, 380, pp. 651-659 (2004).
Millis AJT et al; "In vitro expression of a 38,000 dalton heparin-binding glycoprotein by morphologically differentiated smooth muscle cells". J Cell Physiol, 127, pp. 366-372 (1986).
Nishikawa KC et al; "gp38k (CHI3L1) is a novel adhesion and migration factor for vascular cells". Exp Cell Res, 287, pp. 79-87 (2003).
Nordestgaard BG et al; "Nonfasting trigycerides and risk of myocardial infarction, ischemic heart disease, and death in men and women". JAMA, 298, pp. 299-308 (2007).
Ockene IS et al; "Variability and classification accuracy of serial high-sensitivity C-reactive protein measurements in healthy adults". Clin Chem, 47, pp. 444-450 (2001).
Recklies AD et al; "Inflammatory cytokines induce production of CHI3L1 by articular chondrocytes". J Biol Chem., 280, pp. 41213-41221 (2005).
Recklies AD et al; "The chitinase 3-like protein human cartilage 39 (HC-gp39) stimulates proliferation of human connective-tissue cells and activates both extracellular signal-regulated kinase-and protein kinase B-mediated signalling pathways". Biochem J, 365, pp. 119-126 (2002).
Register TC et al; "Serum YKL-40 Is Associated with Osteoarthritis and Atherosclerosis in Nonhuman Primates". Clinical Chemistry 47, No. 12, 2001, Technical Briefs, pp. 2159-2161.
Renkema GH et al; "Chitotriosidase, a chitinase, and the 39-kDa human cartilage glycoprotein, a chitin-binding lectin, are homologues of family 18 glycosyl hydrolases secreted by human macrophages". Eur J Biochem, 251, pp. 504-509 (1998).
Schnohr P. et al; "Coronary heart disease risk factors ranked by importance for the individual and community. A 21 year follow-up of 12 000 men and women from The Copenhagen City Heart Study". Eur Heart J, 23, pp. 620-626 (2002).
Shackelton LM et al; "Identification of a 38-kDa heparin-binding glycoprotein (gp38k) in differentiating vascular smooth muscle cells as a member of a group of proteins associated with tissue remodelling". J Biol Chem, 270, pp. 13076-13083 (1995).
Amado R.G. et al.; "Wild-Type KRAS Is Required for Panitumumab Efficacy in Patients With Metastatic Colorectal Cancer"; Journal of Clinical Oncology; vol. 26; No. 10; Apr. 1, 2008; pp. 1626-1634.
Andreassen M. et al. Concentrations of the acute phase reactants high-sensitive C-reactive protein and YKL-40 and of interleukin-6 before and after treatment in patients with acromegaly and growth hormone deficiency. Clinical Endocrinology 2007, 67, pp. 909-916.
Andreyev, H.J.N. et al.; "Kirsten ras Mutations in Patients With Colorectal Cancer: the Multicenter "Rascal" Study"; Journal of National Cancer Institute; vol. 90; No. 9; May 6, 1998; pp. 675-684.
Artale, S. et al.; "Mutations of KRAS and BRAF in Primary and Matched Metastatic Sites of Colorectal Cancer"; Journal of Clinical Oncology, 2008 by American Society of Clinical Oncology; vol. 26(25) pp. 4217-4218.
Baselga, J.; "Determinants of RASistance to Anti-Epidermal Growth Factor Receptor Agents"; Journal of Clinical Oncology, vol. 26, No. 10 (Apr. 1, 2008) pp. 1582-1584.
Bokemeyer C. et al.; "Fluorouracil, Leucovorin, and Oxaliplatin With and Without Cetuximab in the First-Line Treatment of Metastatic Colorectal Cancer"; Journal of Clinical Oncology; vol. 27; No. 5, Feb. 10, 2009; pp. 663-671.
Bonneh-Barkay, et al. 2008. "YKL-40, a marker of simian immunodeficiency virus encephalitis, modulates the biological activity of basic fibroblast growth factor" The American Journal of Pathology, vol. 173, No. 1, July, 130-143.
Bonner J.A., et al.; "Radiotherapy plus Cetuximab for Squamous-Cell Carcinoma of the Head and Neck"; New England Journal of Medicine 354,6, Feb. 9, 2006; pp. 567-578.
Brasso K. et. al. Prognostic value of PINP. bone alkaline phosphatase CTX-I, and YKL-40 in patients with metastatic prostate carcinoma. The Prostate 2006, 66, pp. 503-513.
Bray F, et al.; Estimates of Cancer incidence and mortality in Europe in 1995. Eur J. Cancer 2002; 38: 99-166.
Brune K., et al.; "Genetic and Epigenetic Alterations of Familial Pancreatic Cancers"; Cancer Epidemiol Biomarkers Prev 2008; 17(12). Dec. 2008; pp. 3536-3542.
Burris III H.A. et al.; "Improvements in Survival and Clinical Benefit With Gemcitabine as First-Line Therapy for Patients With Advanced Pacreas Cancer: A Randomized Trial"; Journal of Clinical Oncology; Vo. 15; No. 6; Jun. 1997; pp. 2403-2413.
Calonghi et al. 2007. "A new EGFR inhibitor induces apoptosis in colon cancer cells" Biochemical and Biophysical Research Communications, vol. 354, No. 2, Jan. 30, pp. 409-413.
Cascinu S., et al.; Cetuximab plus gemcitabine and cisplatin compared with gemcitabine and cisplatin alone in patients with advanced pancreatic cancer: a randomised, multicentre, phase II trial; Lancet Oncol 2008; 9; pp. 39-44.
Chung K.Y., et al.; "Cetuximab Shows Activity in Colorectal Cancer Patients With Tumors That Do Not Express the Epidermal Growth Factor Receptor by Immunohistochemistry"; Journal of Clinical Oncology; vol. 23; No. 9; Mar. 20, 2005; pp. 1803-1810.
Chupp, G.L. et al. 2007. "A chitinase-like protein in the lung and circulation of patients with severe asthma". The New England Journal of Medicine, 357, 20, Nov. 15, pp. 2016-2027.

(56) References Cited

OTHER PUBLICATIONS

Cintin C, et al. Serum YKL-40 and colorectal cancer. British Journal of Cancer, 1999, 79(9/10), pp. 1494-1499.

Cintin C, et.al. High serum YKL-40 level after surgery for colorectal carcinoma is related to short survival. American Cancer Society, Jul. 15, 2002, vol. 95, No. 2, pp. 267-274.

Cunningham D., et al.; "Cetuximab Monotherapy and Cetuximab plus Irinotecan in Irinotecan-Refractory Metastatic Colorectal Cancer"; New England Journal of Medicine 2004; 351; pp. 337-345.

de Reyniès A. et al.; "KRAS Mutation Signature in Colorectal Tumors Significantly Overlaps With the Cetuximab Response Signature"; Journal of Clinical Oncology; May 1, 2008; 26 (13); pp. 2228-2232.

De Roock W., et al.; "KRAS wild-type state predicts survival and is associated to early radiological response in metastatic colorectal cancer treated with cetuximab"; Annals of Oncology vol. 19, No. 3, Mar. 2008; pp. 508-515.

Dehn H. et al. Plasma YKL-40, as a prognostic tumor marker in recurrent ovarian cancer. Acta Obstet Gynecol Scand 2003, 82, pp. 287-293.

Di Fiore F. et al.; "Clinical relevance of KRAS mutation detection in metastatic colorectal cancer treated by Cetuximab plus chemotherapy"; British Journal of Cancer (2007), 96(8) pp. 1166-1169.

Di Nicolantonio F. et al.; "Wild-Type BRAF Is Required for Response to Panitumumab or Cetuximab in Metastatic Colorectal Cancer"; Journal of Clinical Oncology, vol. 26, No. 35, Dec. 10, 2008; pp. 57055712.

Ferlay J. et al.; "Estimates of the cancer incidence and mortality in Europe in 2006"; Annals of Oncology 18; Feb. 7, 2007; pp. 581-592.

Fiore C.E. and Tamborino C. 2000. "YKL-40 and graft rejection" The American Journal of Medicine, vol. 108, Jun. 1, p. 688-689.

Frattini M., et al.; "PTEN loss of expression predicts cetuximab efficacy in metastatic colorectal cancer patients"; British Journal of Cancer (2007) 97; pp. 1139-1145.

Fredriksson S. et al. Multiplexed proximity ligation assays to profile putative biomarkers relevant to pancreatic and ovarian cancer. Clinical Chemistry 2008, 54:3, pp. 582-589.

Freeman D.J. et al.; "Association of K-ras mutational studies and clincial outcomes in patients with metastatic colorectal cancer receiving panitumumab alone"; Clin Colorectal Cancer 2008; 7; pp. 184-190.

Fukushima N. et al; "Gene expression alterations in the non-neoplastic parenchyma adjacent to infiltrating pancreatic ductal adenocarcinoma"; Modern Pathology (2005); 18; pp. 779-787.

Hecht, J. R., et al; "A Randomized Phase IIIB Trial of Chemotherapy, Bevacizumab, and Panitumumab Compared With Chemotherapy and Bevacizumab Alone for Metastatic Colorectal Cancer"; Journal of Clinical Oncology; vol. 27; No. 5; Feb. 10, 2009; pp. 672-680.

Hormigo A., et al.; YKL-40 and Matrix Metalloproteinase-9 as Potential Serum Biomarkers for Patients with High-Grade Gliomas; Clin Cancer Res 2006, 12 (19) Oct. 1, 2006, pp. 5698-5704.

Jemal A. et al.; "Cancer statistics" 2008. CA Cancer J Clin 2008; 58;71; pp. 71-96.

Jensen B.V. et al.; "High Levels of Serum HER-2/neu and YKL-40 Independently Reflect Aggressiveness of Metastatic Breast Cancer"; Clinical Cancer Research; vol. 9; pp. 4423-4434 2008.

Johansen J.S. et al.; "A New Biochemical Marker for Joint Injury, Analysis of YKL-40 in Serum and Synovial Fluid"; British Journal of Rheumatology 1993; vol. 32; pp. 949-955.

Johansen et al. 2007. "Changes of biochemical markers of bone turnover and YKL-following hormonal treatment for metastatic prostate cancer are related to survival" Clin. Cancer Research, vol. 13, No. 11, Jun. 1, pp. 3244-3249.

Johansen J.S. et al. 2007. "High serum YKL-40 level in a cohort of octogenarians is associated with increased risk of all-cause mortality" Clinical and Experimental Immunology, 151: 260-266.

Johansen J.S. et al. High serum YKL-40 levels in patients with primary breast cancer is related to short recurrence free survival. Breast Cancer Research and Treatment 2003, 80, pp. 15-21.

Johansen J.S. et al. YKL-40 in giant cells and macrophages from patients with giant cell arteritis. Arthritis & Rheumatism, vol. 42, No. 12, Dec. 1999, pp. 2624-2630.

Johansen J.S. et al.; "Diurnal, Weekly, and Long-Time Variation in Serum Concentrations of YKL-40 in Healthy Subjects"; Cancer Epidemiol Biomarkers Prev. 2008; 17(10); Oct. 2008; pp. 2603-2608.

Johansen J.S. et al.; "Elevated Plasma YKL-40 Predicts Increased Risk of Gastrointestinal Cancer and Decreased Survival After Any Cancer Diagnosis in the General Population"; Journal of Clinical Oncology; vol. 27; No. 4; Feb. 1, 2008; pp. 572-578.

Johansen J.S. et al.; "Serum YKL-40 in Healthy Children and Adults. Comparison with Serum and Synovial Fluid Levels of YKL-40 Patients With Osteoarthritis or Trauma of the Knee Joint"; British Journal of Rheumatology 1996; vol. 35; pp. 553-559.

Johansen J.S. Studies on serum YKL-40 as a biomarker in diseases with inflammation, tissue remodelling, fibrosis and cancer. Danish Medical Bulletin, vol. 53, No. 2, May 2006, pp. 172-209.

Johansen J.S., et al; "Postoperative Elevation in Serum YKL-40 in Patients With Colorectal Cancer Is Related to Short Survival"; Proceedings for the American Association for Cancer Research; vol. 41; Mar. 2000; p. 639.

Johansen, J.S. et al. 2008. "High-serum YKL-40 is associated with increased risk of and mortality from gastrointestinal cancer in the general population" Gastrointestinal cancer symposium No. 390, January. Abstract.

Johansen, J.S. et al. Serum YKL-40 concentrations in patients with rheumatoid arthritis: relation to disease activity. Rheumatology, 1999, 38, pp. 618-626.

Johansen, J.S. et al.; "Is YKL-40 a new therapeutic target in cancer?"; Expert Opinion. Ther. Targets (2007) 11(2); pp. 219-234.

Johansen, J.S., et al., "Serum YKL-40 is increased in patients with hepatic fibrosis"; J Hepatol 2000; 32; pp. 911-920.

Jonker et al. 2007. "Cetuximab for the treatment of colorectal cancer" The New England Journal of Medecine, vol. 357, No. 20, pp. 2040-2048.

Kamal S.M. et al. Progression of fibrosis in hepatitis C with and without schistosomiasis: correlation with serum markers of fibrosis. Hepatology, 2006, vol. 43, No. 4, pp. 771-779.

Karapetis C.S. et al.; "K-ras Mutations and Benefit from Cetuximab in Advanced Colorectal Cancer"; The New England Journal of Medicine; Oct. 23, 2008; vol. 359, No. 17; pp. 1757-1765.

Kaynar, et al. 2005. "YKL-40 levels in the cerebrospinal fluid and serum of patients with aneurysmal subarachnoid hemorrhage: preliminary results" Journal of Clinical Neuroscience, 12;7, 754-757.

Khambata-Ford S. et al.; "Expression of Epiregulin and Amphiregulin and K-ras Mutation Status Predict Disease Control in Metastatic Colorectal Cancer Patients Treated With Cetuximab"; Journal of Clinical Oncology; vol. 25; No. 22; Aug. 1, 2007; pp. 3230-3237.

Koutroubakis, I.E., et al.; Increased serum levels of YKL-40 in patients with inflammatory bowel disease; Int J Colorectal Dis (2003); 18: pp. 254-259.

La Montagna, et al. 2003. "Cross-sectional evaluation of YKL-40 serum concentrations in patients with systemic sclerosis. Relationship with clinical and serological aspects of disease". J Rheumatol., 30;2147-51.

Li D. et al.; "Pancreatic cancer" Lancet 2004; 363:1049-59.

Lièvre A. et al.; "KRAS Mutations as an Independent Prognostic Factor in Patients with Advanced Colorectal Cancer Treated With Cetuximab"; Journal of Clinical Oncology; vol. 26; No. 3; Jan. 20, 2008; pp. 374-379.

Lièvre et al. 2006. "KRAS mutation status is predictive of response to cetuximab therapy in colorectal cancer" Cancer research, American Association for Cancer Research. vol. 66, No. 8, Apr. 15, pp. 3992-3995.

Lim J.E. et al.; Prognostic factors following curative resection for pancreatic adenocarcinoma; a population based, linked database analysis of 396 patients. Ann Surg 2003; 237:74-85.

Madazli, et al. 2008. "Chitotriosidase and YKL-40 in normal and pre-eclamptic pregnancies" International Journal of Gynecology and Obstetrics. 100, 239-243.

(56) References Cited

OTHER PUBLICATIONS

Malumbres M., et al.; "RAS oncogenes: the first 30 years"; Nature Reviews, vol. 3; Jun. 2003; pp. 7-13.
Messersmith W.A. et al.; "Targeting EGFR in Colorectal Cancer"; N. Engl. Journal of Medicine 359:17; Oct. 23, 2008; pp. 1834-1836.
Mylin, et al. 2008. "High serum YKL-40 concentration is associated with severe bone disease in newly diagnosed multiple myeloma patients" European Journal of Haematology, 310-317.
Nielsen, et al. 2008. "A BMI-independent marker of type 2 diabetes" Diabetes, vol. 57, November, 3078-3082.
Nøjgaard, C et al. 2003. "Serum levels of YKL-40 and PIIINP as prognostic markers in patients with alcoholic liver disease". Journal of Hepatology 39; 179-186.
Pfeiffer P. et al.; "Cetuximab and irinotecan as third line therapy in patients with advanced colorectal cancer after failure of irinotecan, oxaliplatin and 5-fluorouracil"; Acta Oncologica; 46:5; 2007; pp. 697-701.
Philip P.A. et al. Phase III study of gemcitabine (G) plus cetuximab (C) versus gemcitabinie in patients (pts) with locally advanced or metastatic pancreatic adenocarcinoma (PC): SWOG S0205 study; Proc Am Soc Clin Oncol; 25 (abstr 409).
Rathcke C.N. et al.; "YKL-40, a biomarker of inflammation, is elevated in patients with type 2 diabetes and is related to insulin resistance"; Inflamm. Res. 55 (2006); pp. 53-59.
Rathcke et al. 2010. "Plasma YKL-40 levels are elevated in patients with chronic heart failure" Scandinavian Cardiovascular Journal, 2010; 44: 92-99.
Rathcke, C.N. and Vestergaard, H. 2006. "YKL-40, a new inflammatory marker with relation to insulin resistance and with a role in endothelial dysfunction and atherosclerosis". Inflammation Research, 55, p. 221-227.
Roslind et al. 2008. "High serum levels of YKL-40 in patients with squamous cell carcinoma of the head and neck are associated with short survival" Int. J. Cancer, vol. 122, No. 4, February, pp. 857-863.
Royston, P. 1991 "Constructing time-specific reference ranges" Statistics in medicine, vol. 10, No. 5, pp. 675-690.
Saltz L.B. et al.; "Phase II Trial of Cetuximab in Patients With Refractory Colorectal Cancer That Express the Epidermal Growth Factor Receptor"; Journal of Clinical Oncology; vol. 22; No. 7; Apr. 1, 2004; pp. 1201-1207.
Schmidt, H. et al.; "Serum YKL-40 Predicts Relapse-Free and Overall Survival in Patients With American Joint Committee on Cancer Stage I and II Melanoma"; Journal of Clinical Oncology; vol. 24, No. 5, Feb. 10, 2006; pp. 798-804.
Tol J. et al.; "Chemotherapy, Bevacizumab, and Cetuximab in Metastatic Colorectal Cancer"; The New England Journal of Medicine; Feb. 5, 2009; vol. 360; No. 6; pp. 563-572.
Tsuji, et al. 2002. "Analysis of chondrex (YKL-40, HC gp-39) in the cerebrospinal fluid of patients with spine disease" SPINE, vol. 27, 7, 732-735.
van Cutsem, E., et al.; "Open-Label Phase III Trial of Panitumumab Plus Best Supportive Care Compared With Best Supportive Care Alone in Patients With Chemotherapy-Refractory Metastatic Colorectal Cancer"; Journal of Clinical Oncology; vol. 25; No. 13; May 1, 2007; pp. 1658-1664.
Vincenzi B. et al.; "Cetuximab and irinotecan as third-line therapy in advanced colorectal cancer patients: a single centre phase II trial"; British Journal of Cancer (2006) 94(6), pp. 792-797.
Vind, I et al. 2003. "Serum YKL-40, a Potential New Marker of Disease Activity in Patients with Inflammatory Bowel Disease" Scandinavian Journal of Gastroenterology 38:6, 599-605.
Wang et al. 2008. "YKL-40 a new biomarker in patients with acute coronary syndrome or stable coronary artery disease" Scandinavian Cardiovascular Journal, 42:5, 295-302.
Winer E. et al.; "Clinical Cancer Advances 2008: Major Research Advances in Cancer Treatment, Prevention, and Screening—A Report From the American Society of Clinical Oncology"; Journal of Clinical Oncology; vol. 27; No. 5; Feb. 10, 2008; pp. 812-826.
Wong R. et al.; "Using Predictive Biomarkers to Select Patients With Advanced Colorectal Cancer for Treatment With Epidermal Growth Factor Receptor Antibodies"; Journal of Clinical Oncology; vol. 26; No. 35; Dec. 10, 2008; pp. 5668-5670.
Zheng, et al. 2005. "Determination of serum levels in YKL-40 and hyaluronic acid and in patients with hepatic fibrosis due to *Schistosomiasis japonica* and appraisal of their clinical value" Acta Tropica 96, 148-152.
Østergaard, et al. 2002. "YKL-40 is elevated in cerebrospinal fluid from patients with purulent meningitis" Clinical and Diagnostic Laboratory Immunology, May, p. 598-604.
Bojesen et al., "Plasma YKL-40 levels in healthy subjects from the general population," Clin Chim Acta. 412:709-712 (2011).
Harutyunyan et al., "The inflammatory biomarker YKL-40 as a new prognostic marker for all-cause mortality in patients with heart failure," Immunobiology. 217:652-656 (2012).
Harutyunyan et al., "Serum YKL-40 predicts long-term mortality in patients with stable coronary disease: A prognostic study with the Claricor trial," Immunobiology. 218:945-951 (2013).
Mygind et al., "The inflammatory biomarker YKL-40 at admission is a strong predictor of overall mortality," J Intern Med. 273:205-216 (2013).

\* cited by examiner

A

B

```
                         SEQUENCE LISTING

<160> NUMBER OF SEQ ID NOS: 2

<210> SEQ ID NO 1
<211> LENGTH: 1741
<212> TYPE: DNA
<213> ORGANISM: Homo sapiens

<400> SEQUENCE: 1
ctaggtagct ggcaccagga gccgtgggca agggaagagg ccacaccctg ccctgctctg      60
ctgcagccag aatgggtgtg aaggcgtctc aaacaggctt tgtggtcctg gtgctgctcc     120
agtgctgctc tgcatacaaa ctggtctgct actacaccag ctggtcccag taccgggaag     180
gcgatgggag ctgcttccca gatgcccttg accgcttcct ctgtacccac atcatctaca     240
gctttgccaa tataagcaac gatcacatcg acacctggga gtggaatgat gtgacgctct     300
acggcatgct caacacactc aagaacagga cccccaacct gaagactctc ttgtctgtcg     360
gaggatggaa ctttgggtct caaagatttt ccaagatagc ctccaacacc cagagtcgcc     420
ggactttcat caagtcagta ccgccattcc tgcgcaccca tggctttgat gggctggacc     480
ttgcctggct ctaccctgga cggagagaca acagcatttt taccacccta atcaaggaaa     540
tgaaggccga atttataaag gaagcccagc cagggaaaaa gcagctcctg ctcagcgcag     600
cactgtctgc ggggaaggtc accattgaca gcagctatga cattgccaag atatcccaac     660
acctggattt cattagcatc atgacctacg attttcatgg agcctggcgt gggaccacag     720
gccatcacag tcccctgttc cgaggtcagg aggatgcaag tcctgacaga ttcagcaaca     780
ctgactatgc tgtgggtac atgttgaggc tgggggctcc tgccagtaag ctggtgatgg     840 gcatcccac cttcggagg agcttcactc tggcttcttc tgaactggt gttggagccc        900 caatctcagg accgggaatt ccaggccggt tcaccaagga ggcagggacc cttgcctact     960
atgagatctg tgacttcctc cgcggagcca cagtccatag aaccctcggc cagcaggtcc    1020
cctatgccac caagggcaac cagtgggtag gatacgacga ccaggaaagc gtcaaaagca    1080
aggtgcagta cctgaaggat aggcagctgg caggcgccat ggtatgggcc ctggacctgg    1140
atgacttcca gggctcctcc tgcggccagg atctgcgctt ccctctcacc aatgccatca    1200
```

```
aggatgcact cgctgcaacg tagccctctg ttctgcacac agcacggggg ccaaggatgc    1260
cccgtccccc tctggctcca gctggccggg agcctgatca cctgccctgc tgagtcccag    1320
gctgagcctc agtctccctc ccttggggcc tatgcagagg tccacaacac acagatttga    1380
gctcagccct ggtgggcaga gaggtaggga tggggctgtg gggatagtga ggcatcgcaa    1440
tgtaagactc gggattagta cacacttgtt gatgattaat ggaaatgttt acagatcccc    1500
aagcctggca agggaatttc ttcaactccc tgcccctag ccctccttat caaaggacac    1560
cattttggca agctctatca ccaaggagcc aaacatccta caagacacag tgaccatact    1620
aattataccc cctgcaaagc cagcttgaaa ccttcactta ggaacgtaat cgtgtcccct    1680
atcctacttc cccttcctaa ttccacagct gctcaataaa gtacaagagt ttaacagtgt    1740
g                                                                   1741

<210> SEQ ID NO 2
<211> LENGTH: 383
<212> TYPE: PRT
<213> ORGANISM: Homo sapiens

<400> SEQUENCE: 2

Met Gly Val Lys Ala Ser Gln Thr Gly Phe Val Val Leu Val Leu Leu
1               5                   10                  15

Gln Cys Cys Ser Ala Tyr Lys Leu Val Cys Tyr Tyr Thr Ser Trp Ser
            20                  25                  30

Gln Tyr Arg Glu Gly Asp Gly Ser Cys Phe Pro Asp Ala Leu Asp Arg
        35                  40                  45

Phe Leu Cys Thr His Ile Ile Tyr Ser Phe Ala Asn Ile Ser Asn Asp
    50                  55                  60

His Ile Asp Thr Trp Glu Trp Asn Asp Val Thr Leu Tyr Gly Met Leu
65                  70                  75                  80

Asn Thr Leu Lys Asn Arg Asn Pro Asn Leu Lys Thr Leu Leu Ser Val
                85                  90                  95

Gly Gly Trp Asn Phe Gly Ser Gln Arg Phe Ser Lys Ile Ala Ser Asn
            100                 105                 110

Thr Gln Ser Arg Arg Thr Phe Ile Lys Ser Val Pro Pro Phe Leu Arg
        115                 120                 125

Thr His Gly Phe Asp Gly Leu Asp Leu Ala Trp Leu Tyr Pro Gly Arg
    130                 135                 140

Arg Asp Lys Gln His Phe Thr Thr Leu Ile Lys Glu Met Lys Ala Glu
145                 150                 155                 160

Phe Ile Lys Glu Ala Gln Pro Gly Lys Lys Gln Leu Leu Leu Ser Ala
                165                 170                 175

Ala Leu Ser Ala Gly Lys Val Thr Ile Asp Ser Ser Tyr Asp Ile Ala
            180                 185                 190

Lys Ile Ser Gln His Leu Asp Phe Ile Ser Ile Met Thr Tyr Asp Phe
        195                 200                 205

His Gly Ala Trp Arg Gly Thr Thr Gly His His Ser Pro Leu Phe Arg
    210                 215                 220

Gly Gln Glu Asp Ala Ser Pro Asp Arg Phe Ser Asn Thr Asp Tyr Ala
225                 230                 235                 240

Val Gly Tyr Met Leu Arg Leu Gly Ala Pro Ala Ser Lys Leu Val Met
                245                 250                 255

Gly Ile Pro Thr Phe Gly Arg Ser Phe Thr Leu Ala Ser Ser Glu Thr
            260                 265                 270
```

-continued

```
Gly Val Gly Ala Pro Ile Ser Gly Pro Gly Ile Pro Gly Arg Phe Thr
        275                 280                 285

Lys Glu Ala Gly Thr Leu Ala Tyr Tyr Glu Ile Cys Asp Phe Leu Arg
        290                 295                 300

Gly Ala Thr Val His Arg Thr Leu Gly Gln Gln Val Pro Tyr Ala Thr
305                 310                 315                 320

Lys Gly Asn Gln Trp Val Gly Tyr Asp Asp Gln Glu Ser Val Lys Ser
                325                 330                 335

Lys Val Gln Tyr Leu Lys Asp Arg Gln Leu Ala Gly Ala Met Val Trp
                340                 345                 350

Ala Leu Asp Leu Asp Asp Phe Gln Gly Ser Phe Cys Gly Gln Asp Leu
        355                 360                 365

Arg Phe Pro Leu Thr Asn Ala Ile Lys Asp Ala Leu Ala Ala Thr
370                 375                 380
```

YKL-40 AS A GENERAL MARKER FOR NON-SPECIFIC DISEASE

CROSS-REFERENCE TO RELATED APPLICATIONS

This application is the U.S. national stage filing under 35 U.S.C. §371 of International Application No. PCT/DK2009/050014, filed on Jan. 22, 2009, which claims benefit of Danish Patent Application No. PA 2008 00089, filed on Jan. 23, 2008, Danish Patent Application No. PA 2008 01292, filed on Sep. 15, 2008, Danish Patent Application No. PA 2008 01293, filed on Sep. 15, 2008, and Danish Patent Application No. PA 2008 01294, filed on Sep. 15, 2008, each of which is incorporated by reference.

FIELD OF INVENTION

The present invention relates to a method of diagnosing the presence of a non-specific disease or disorder in a subject, wherein a determined level of YKL-40 above a reference level indicates the presence of a non-specific disease or disorder. The subject may suffer from a variety of diseases or disorders. The present invention furthermore relates to a method for classifying the severity of a non-specific disease or disorder in a subject, wherein a determined level of YKL-40 above or below one or more reference levels gives the severity of said non-specific disease or disorder. The present invention further relates to a kit and a device that may be used in the method of the present invention comprising means for measuring the level of YKL-40 in a sample; and means for comparing the measured level of YKL-40 with at least one reference level of YKL-40.

BACKGROUND OF INVENTION

Whenever an illness, a disease or one or more symptoms are to be treated, it requires a diagnosis of the underlying disease or disorder. Many symptoms can arise from several diseases, including both physical and mental diseases. Therefore the diagnosis of the disease is of paramount importance for the succeeding treatment. The outcome of a treatment can in many cases depend on the progression of the disease, and therefore on the time elapsed prior to diagnosis, early intervention may be very important. However, in order for a patient to seek medical assistance at least some symptoms needs to be present. Very often a disease may develop without the patient being aware of this, as for example in various cancer diseases and lifestyle diseases, such as e.g. atherosclerosis, coronary heart disease, diabetes, hypertension, liver fibrosis, chronic obstructive lung disease, etc.

Some diseases can be more effectively cured or even avoided if preventive steps such as lifestyle changes are introduced in time. Therefore it has also become increasingly common to participate in health screenings. Health screenings very often do not have any symptoms to rely on as a starting point. To establish a diagnosis for a patient, whether symptoms already exist or it is in relation to a health screening, the physician needs a starting point for the elucidation.

Previously the "Erythrocyte sedimentation rate" (also denoted sedimentation rate) has been widely used as an indicator of the presence of inflammation. The sedimentation rate is the rate at which red blood cells precipitate in a period of 1 hour. When an inflammatory process is present, the high proportion of fibrinogen in the blood causes red blood cells to stick to each other. The sedimentation rate is increased by any cause or focus of inflammation. The basal sedimentation rate is slightly higher in women and tends to rise with age. The usefulness of the sedimentation rate in asymptomatic persons is however limited by its low sensitivity and specificity, but it has been used as a sort of sickness index, when a moderate suspicion of disease was present.

At present the biomarker C-reactive protein (CRP) has mostly taken over from the previously used sedimentation rate in initial screenings for inflammation. CRP is an indicator of acute or chronic inflammation or infection, and is therefore a test of value in medicine, reflecting the presence and intensity of inflammation, although an elevation in C-reactive protein is not the telltale diagnostic sign of any one condition. Conditions which can cause a positive response in the serum CRP level are for example rheumatoid arthritis, lupus, rheumatic fever, cancer, hearth disease, cardiovascular disease, inflammatory bowel disease, and bacterial or viral infections. However not all patients with these diseases have an elevated serum CRP level, and for these patients the serum CRP level cannot be used as a sickness-index.

SUMMARY OF INVENTION

The present invention as described herein relates to a method for diagnosing the presence of a non-specific disease or disorder in a subject, said method comprising
  i) determining the level of YKL-40 in a sample obtained from the subject; and
  ii) comparing said level of YKL-40 with a reference level of YKL-40;
wherein a level of YKL-40 in the sample above the reference level indicates the presence of a non-specific disease or disorder. Preferably the reference level of YKL-40 is an average level obtained by measuring the YKL-40 levels in samples from healthy individuals. Alternatively, the reference level of YKL-40 is a previously determined level of YKL-40 from the same subject, wherein a level of YKL-40 in the sample increased by a factor of 1.10 compared to the previously determined level of YKL-40 indicates the presence of a non-specific disease or disorder.

The present invention furthermore relates to a method for classifying the severity of a non-specific disease or disorder in a subject, said method comprising
  i) determining the level of YKL-40 in a sample obtained from the subject; and
  ii) comparing the level of YKL-40 with one or more reference levels of YKL-40;
wherein the severity of said non-specific disease or disorder is deduced from said comparison. Preferably the one or more reference levels of YKL-40 may be provided by measuring the YKL-40 levels in samples from healthy individuals. Alternatively, the reference level of YKL-40 may be previously determined levels of YKL-40 from the same subject.

The present invention as described herein further relates to a device for the diagnosis of the presence of a non-specific disease or disorder, wherein the device comprises means for measuring the level of YKL-40 in a sample; and means for comparing the measured level of YKL-40 with at least one reference level of YKL-40. In a preferred embodiment of the invention the device comprises a single reference level, representing a cut-off value.

Furthermore, the present invention as described herein relates to a kit of parts comprising i) means for measuring the level of YKL-40 in a sample; ii) means for comparing the measured level of YKL-40 with at least one reference level of YKL-40; and iii) optionally instructions on how to age adjust the reference level of YKL-40, according to the age of the subject providing the sample.

DETAILED DESCRIPTION OF THE INVENTION

Figure 1:
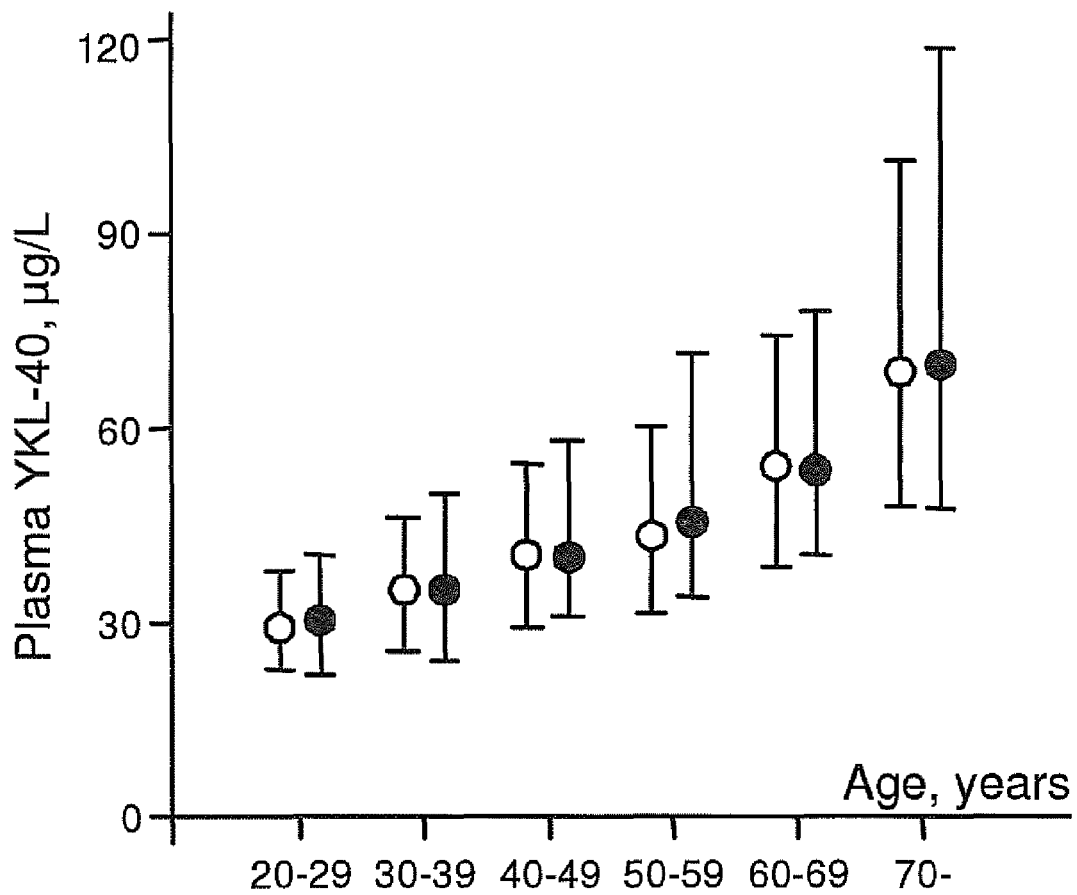
FIG. 1. Plasma concentrations of YKL-40 in 2116 healthy women and 1494 healthy men according to age and sex. The participants had no known disease at the time of blood sampling in 1991-1994 and remained healthy during the 16 years follow-up period (i.e. none were dead or had developed cancer, ischaemic cardiovascular disease, liver disease, diabetes, chronic obstructive pulmonary disease, asthma, rheumatoid arthritis, inflammatory bowel disease, and pneumonia). The median plasma YKL-40 in these healthy participants was 42 μg/L (2.5%-97.5% percentile range: 14-168 μg/L; 90% percentile 92 μg/L; 95% percentile 124 μg/L). Plasma YKL-40 levels increased in both sexes with increasing age (trend test p<0.0001). Spearman's rho correlation between plasma YKL-40 and age was 0.41 (p<0.0001). There was no difference between plasma YKL-40 in women and men (Mann-Whitney U; p=0.27).

The present inventors have surprisingly found that the YKL-40 level can be used as a general biomarker giving an indication of the presence of a non-specific disease or disorder. Accordingly, by the method according to the present invention the YKL-40 level can be used to diagnose the presence of a non-specific disease or disorder.

The following definitions are provided to simplify discussion of the invention. They should not, therefore, be construed as limiting the invention, which is defined in scope by the appended claims and the specification in its entirety.

The terms "a non-specific disease or disorder", "a non-specific disease" or "a non-specific disorder", as used herein, are intended to mean any disease or disorder, such as for example any one or more diseases or disorders that are yet to be specifically diagnosed as a specific disease or disorder. A subject having a non-specific disease or disorder may be distinguished from the general population by not being healthy, i.e. as having some form of a disease or disorder. Accordingly, the diagnosis of the presence of a non-specific disease or disorder does not provide information about which specific disease or disorder is present in the subject.

The term "general biomarker", as used herein, is intended to mean a biomarker that gives an indication of the presence of a disease or disorder in a subject, as opposed to the subject being healthy. A general biomarker does not give information about or a diagnosis of a specific disease or disorder in a subject, but is used in an initial screening. The absence of the general biomarker, such as e.g. a level below detectable levels, or below a predefined cut-off value, is however not to be construed as an evidence of no disease or no disorder present in a subject. A general biomarker may be used to give the first indication of the presence of a disease or disorder, as a starting point for further diagnosing of a specific disease.

An example of a widely used general biomarker for inflammation is serum C-reactive protein (CRP). CRP is often used in connection with an initial screening, and is for instance used as a rough indicator of risk of heart disease, cardiovascular disease, bacterial infections, viral infections etc. However, some patients with diseases or disorders will not have and increase in the serum CRP level, and the CRP level can therefore not be used as a sickness index for all patients with these diseases.

Before CRP became widely used and well-known, the Erythrocyte Sedimentation Rate (often referred to as Sedimentation Rate) was used in an initial screening as a non-specific measure of inflammation, i.e. as a sickness index.

The method according to the present invention provides a new general biomarker in the form of the YKL-40 level and provides a method of diagnosing the presence of a non-specific disease or disorder or classifying the severity of such a non-specific disease or disorder. It has furthermore been found that YKL-40 can be used not only to determine whether a non-specific disease or disorder is present but also to determine the state of disease, i.e. the severity of a non-specific disease or disorder. In other words the YKL-40 level has been found to be useful as a sickness index. Accordingly, YKL-40 can be used to classify whether a disease or disorder in a subject evolves towards a more or a less severe state of the disease or disorder. The present inventors have found the YKL-40 to be a more broad general biomarker than serum CRP.

Accordingly, a first aspect of the present invention relates to a method for diagnosing the presence of a non-specific disease or disorder in a subject, said method comprising
iii) determining the level of YKL-40 in a sample obtained from the subject; and
iv) comparing said level of YKL-40 with a reference level of YKL-40;
wherein a level of YKL-40 in the sample above the reference level indicates the presence of a non-specific disease or disorder.

The method according to the present is relevant for diagnosing the presence of any disease or disorder, such as e.g. any one or more diseases or disorders. Said diseases or disorders may for instance be any disease of disorder for which the YKL-40 level is increased.

It has been found that the serum or plasma YKL-40 level in an individual is stable over long time, and independent of diurnal and weekly changes; it has furthermore been found that the level is independent of at least 20 minutes of exercise. Accordingly, one measurement of the serum or plasma YKL-40 level in an individual can be used in the method according to the invention. Preferably, the sample may be obtained from a subject that for example have abstained from heavy alcohol consumption the previous day and that for example do not have evident symptoms of e.g. bacterial infections. If necessary a second or further sample may be obtained at a later time point (e.g. after 2 weeks) to confirm the results of the first determined level of YKL-40.

It is to be emphasised that increased levels of YKL-40, such as e.g. in plasma or serum, can reflect several and diverse types of diseases and disorders, and that such increased levels of YKL-40 is not generally seen in healthy subjects. Therefore the YKL-level can be used as a sickness index according to the present invention.

A second aspect of the present invention relates to the use of YKL-40 as a biomarker for the presence of a non-specific disease or disorder. Further details for this aspect of the present invention will be apparent from the text describing the above mentioned method of the invention. Accordingly, any features mentioned in relation to the method of the invention apply mutatis mutandis to the use of YKL-40 as a biomarker for the presence of a non-specific disease or disorder.

The present invention furthermore relates to a method for determining the presence of an increased YKL-40 level in a subject, such as e.g. an increased plasma or serum YKL-40 level, said method comprising
v) determining the level of YKL-40 in a sample obtained from the subject; and
vi) comparing said level of YKL-40 with a reference level of YKL-40;
wherein a level of YKL-40 in the sample above the reference level indicates the presence of an increased YKL-40 level in said subject. The reference level may be any reference level as described herein, and especially as described in the section "reference levels". This method is preferably used for diagnosing the presence of a non-specific disease or disorder, such as e.g. any disease or disorder, in a subject, as described herein, A third aspect of the present invention relates to a method for diagnosing the presence of a non-specific disease or disorder in a subject, said method comprising
i) determining the level of YKL-40 in a sample obtained from the subject; and
ii) comparing said level of YKL-40 with a reference level of YKL-40, said reference level being a previously determined level of YKL-40 from the same subject;
wherein a level of YKL-40 in the sample increased to a factor of 1.10 compared to the reference level of YKL-40 indicates the presence of a non-specific disease or disorder. Further details for this third aspect of the present invention will be apparent from the text describing the above mentioned first aspect of the invention. Accordingly, any features mentioned in relation to the first aspect of the invention apply mutatis mutandis to this third aspect of the invention, unless otherwise stated.

A fourth aspect of the present invention relates to a method for classifying the severity of a non-specific disease or disorder in a subject, said method comprising
iii) determining the level of YKL-40 in a sample obtained from the subject; and
iv) comparing the level of YKL-40 with one or more reference levels of YKL-40;
wherein the severity of said non-specific disease or disorder is deduced from said comparison. Preferably the one or more reference levels of YKL-40 may be provided by measuring the YKL-40 levels in samples from healthy individuals. Alternatively, the reference level of YKL-40 may be previously determined levels of YKL-40 from the same subject. Such types of reference levels is further described herein below and especially in the below section "reference levels".

The present inventors have surprisingly found that the YKL-40 level can be used in this fourth aspect of the invention as a biomarker for the classification of the severity of a non-specific disease or disorder by comparison with one or more reference levels of YKL-40. The present inventors have furthermore found that the YKL-40 level can be used as a marker for keeping track of the development of a disease or disorder, i.e. whether the disease or disorder evolve towards a more or a less severe stage of a diseases or disorder, hereby repeatedly and/or continuously classifying the severity of a disease or disorder over time. This is especially interesting and feasible when an YKL-40 measurement in a subject is compared to one or more reference levels which are previously obtained measurement from the same subject. Accordingly, by the methods according to the present invention the YKL-40 level can be used to not only classify the severity of a disease or disorder in a subject, both also to classify and follow the severity of a disease or disorder.

Patients with the same disease can have marked differences in the disease severity (i.e. different grades of how serious the disease is). The terms "severe stage", "severity", "less severe" and "more severe", as used herein, are intended to mean a graduation of severity according to for example prognosis for being cured, prognosis for survival, prognosis for disease progression, or according to different predetermined stages of diseases. Such stages may be according to various symptoms, and/or traditionally measureable levels of biomarkers, physical functions etc. When focusing on the development of a disease in one and same subject, then a more severe stage refers to a worsening of the disease, whereas a less severe stage than previously determined refers to a bettering of the disease, e.g. due to a satisfactory treatment regime.

Further details for this fourth aspect of the present invention will be apparent from the text describing the above mentioned first or third aspects of the invention. Accordingly, any features mentioned in relation to the first or third aspect of the invention apply mutatis mutandis to this fourth aspect of the invention, unless otherwise stated.

A fifth aspect of the present invention relates to the use of YKL-40 as a biomarker for classifying the severity of a disease or disorder. Further details for this aspect of the present invention will be apparent from the text describing the above mentioned methods of the invention. Accordingly, any features mentioned in relation to the methods of the invention apply mutatis mutandis to the use of YKL-40 as a biomarker for classifying the severity of a disease or disorder.

The methods according to the present invention can be used to identify the presence or the severity of diseases that also may be identified by CRP, but can furthermore be used to identify diseases that will not give a response in the CRP level. Accordingly, in one embodiment of the present invention, the non-specific disease or disorder is one or more diseases or disorders or a group of diseases or disorders that do not provide an elevated C-reactive protein level.

It is further envisaged that the methods according to the present invention, may be used as a diagnostic tool in connection with companion diagnostic test in personalized medicine. This could for instance be in relation to YKL-40 ligands, or any other type of active compounds used to treat a disease or disorder.

The term "ameliorate", as used herein, is intended to mean to improve or make better; in association with a disease state a lessening in the severity or progression of a disease state, including remission or cure thereof, alternatively the perceived lessening of severity such as lessening of associated pain.

The term "antibody", as used herein, is intended to mean Immunoglobulin molecules and active portions or fragments of immunoglobulin molecules such as Fab and F(ab').sub.2 which are capable of binding an epitopic determinant of the YKL-40 protein. Antibodies are for example intact immunoglobulin molecules or fragments thereof retaining the immunologic activity. The term "antigen", as used herein, is intended to mean an immunogenic full-length or fragment of a YKL-40 molecule.

The term "biological sample", as used herein, is intended to mean a sample obtained from a subject or individual.

The term "biomarker", as used herein, is intended to mean a molecular indicator of a specific biological property, such as a pathological or physiological state.

The terms "disease" and/or "disorder", as used herein, is intended to mean an illness, injury, or disorder in a subject or individual. A disorder is often an illness or injury of a congenital type.

The terms "subject" and/or "individual", as used herein, is intended to mean a single member of a species, herein preferably a mammalian species. The term "mammal", as used herein, is intended to include both humans and non-humans. The term "patient" as used herein, is intended to mean any individual suffering from a disease or disorder.

The term "hnRNA", as used herein, means heteronuclear RNA. The term "mAb", as used herein, means monoclonal antibody. The term "mRNA", as used herein, means messenger RNA. The term "RNA", as used herein, means any type of RNA originating alternatively isolated from nature or synthesized. The term "substantially pure", as used herein to describe YKL-40, refers to the substantially intact molecule which is essentially free of other molecules with which YKL-40 may be found in nature.

YKL-40

YKL-40 is named based on its three N-terminal amino acids Tyrosine (Y), Lysine (K) and Leucine (L) and its molecular mass of about 40 kDa (Johansen et al. 1992). The complete amino acid (SEQ ID NO: 2) and coding sequence (SEQ ID NO: 1) of human YKL-40 is found in GenBank under Accession number: M80927. Human YKL-40 contains a single polypeptide chain of 383 amino acids and is a phylogenetically highly conserved heparin- and chitin-binding plasma glycoprotein. The sequence identity between human YKL-40 and homologs from several other mammals is: pig (84% sequence identity), cow (83%), goat (83%), sheep (83%), guinea pig, rat (80%), and mouse (73%). YKL-40 is a member of "mammalian chitinase-like proteins", but has no chitinase activity. YKL-40 expression in vitro is absent in normal human monocytes but strongly induced during late stages of macrophage differentiation by activated monocytes and neutrophils, by vascular smooth muscle cells, cancer cells and arthritic chondrocytes. In vivo YKL-40 mRNA and protein are expressed by a subpopulation of macrophages in tissues with inflammation such as atherosclerotic plaques, arthritic vessels of individuals with giant cell arthritis, inflamed synovial membranes, sarcoid lesions, and by peritumoral macrophages.

The molecular processes governing the induction of YKL-40 and its precise functions are unknown. YKL-40 is a secreted protein suggesting that its sites of actions are most likely to be extracellular; however, specific cell-surface or soluble receptors for YKL-40 have not yet been identified. YKL-40 is a growth factor for fibroblasts and chondrocytes, acts synergistically with IGF-1, is regulated by TNF and IL-6, and requires sustained activation of NF-kappaB (Recklies et al., 2002, Ling et al., 2004, Recklies et al., 2005). YKL-40 treatment of fibroblasts can counteract the inflammatory response to TNF and IL-1 by phosphorylation of AKT, thereby attenuating ASK1 mediated signaling pathways. This leads to decreased levels of metalloproteinase and IL-8 expression (Recklies et al., 2002, Ling et al., 2004, Recklies et al., 2005). Furthermore, YKL-40 binds to collagen types I, II and III and modulates the rate of type I collagen fibril formation (Bigg et al., 2006). These observations suggest that YKL-40 may play a protective role in inflammatory environments, limiting degradation of the extracellular matrix and thereby controlling tissue remodeling. YKL-40 also acts as a chemo-attractant for endothelial cells, stimulates their migration and promotes migration and adhesion of vascular smooth muscle cells (Millis et al., 1986, Nishikawa et al., 2003; Shackelton et al., 1995) suggesting a role in angiogenesis. YKL-40 is also a growth factor for fibroblasts and has an anti-catabolic effect preserving extracellular matrix during tissue remodeling (De Ceunicnck et al., 2001, Recklies et al., 2002, Ling et al., 2004, Recklies et al., 2005). In addition, macrophages in atherosclerotic plaques express YKL-40 mRNA, particularly macrophages that have infiltrated deeper in the lesion, and the highest YKL-40 expression is found in macrophages in the early lesion of atherosclerosis (Boot et al., 1999). Furthermore YKL-40 can be regarded as an acute phase protein, since its plasma or serum concentration is increased in several inflammatory diseases.

Cellular receptors mediating the biological effects of YKL-40 are not known, but the activation of cytoplasmic signal-transduction pathways suggests that YKL-40 interacts with signaling components on the cell membrane.

It is an object of the present invention to detect any transcriptional product of the YKL-40 gene. A transcriptional product of the gene may thus be hnRNA, mRNA, full length protein, fragmented protein, or peptides of the YKL-40 protein. It is understood that one or more proteins, RNA transcripts, fragments and/or peptides may be detected simultaneously. It is furthermore an aspect of the present invention to detect transcriptional products by any means available such as by immunoassays such as antibody detection of the YKL-40 protein, fragments or peptides hereof, as well as by detection by PCR based assays such as detection of RNA by RT-PCR.

Detection of YKL-40

Peptides and polynucleotides of the invention include functional derivatives of YKL-40, YKL-40 peptides and nucleotides encoding therefore. By "functional derivative" is meant the "fragments," "variants," "analogs," or "chemical derivatives" of a molecule. A "fragment" of a molecule, such as any of the DNA sequences of the present invention, includes any nucleotide subset of the molecule. A "variant" of such molecule refers to a naturally occurring molecule substantially similar to either the entire molecule, or a fragment thereof. An "analog" of a molecule refers to a non-natural molecule substantially similar to either the entire molecule or a fragment thereof.

A molecule is said to be "substantially similar" to another molecule if the sequence of amino acids in both molecules is substantially the same. Substantially similar amino acid molecules will possess a similar biological activity. Thus, provided that two molecules possess a similar activity, they are considered variants as that term is used herein even if one of the molecules contains additional amino acid residues not found in the other, or if the sequence of amino acid residues is not identical.

Further, a molecule is said to be a "chemical derivative" of another molecule when it contains additional chemical moieties not normally a part of the molecule. Such moieties may improve the molecule's solubility, absorption, biological half-life, etc. The moieties may alternatively decrease the toxicity of the molecule, eliminate or attenuate any undesirable side effect of the molecule, etc. Moieties capable of mediating such effects are disclosed, for example, in Remington's Pharmaceutical Sciences, 16th Ed., Mack Publishing Co., Easton, Pa., 1980.

Minor modifications of the YKL-40 primary amino acid sequence may result in proteins and peptides that have substantially similar activity as compared to the YKL-40 peptides described herein. Such modifications may be deliberate, as by site-directed mutagenesis, or may be spontaneous. All of the peptides produced by these modifications are included herein as long as the biological activity of YKL-40 still exists. Further, deletion of one or more amino acids can also result in a modification of the structure of the resultant molecule without significantly altering its biological activity. This can lead to the development of a smaller active molecule which would have broader utility. For example, one can remove amino or carboxy terminal amino acids which may not be required for the enzyme to exert the desired catalytic or antigenic activity.

Either polyclonal or monoclonal antibodies may be used in the immunoassays and therapeutic methods of the invention described below. Some anti-YKL-40 antibodies are available commercially or may alternatively be raised as herein described or known in the art. Polyclonal antibodies may be raised by multiple subcutaneous or intramuscular injections of substantially pure YKL-40 or antigenic YKL-40 peptides into a suitable non-human mammal. The antigenicity of YKL-40 peptides can be determined by conventional techniques to determine the magnitude of the antibody response of an animal which has been immunized with the peptide. Generally, the YKL-40 peptides which are used to raise the anti-YKL-40 antibodies should generally be those which induce production of high titers of antibody with relatively high affinity for YKL-40. In one embodiment of the invention the YKL-40 level is determined by use of a dipstick.

If desired, the immunizing peptide may be coupled to a carrier protein by conjugation using techniques which are well-known in the art. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g. a mouse or a rabbit). Because YKL-40 may be conserved among mammalian species, use of a carrier protein to enhance the immunogenicity of YKL-40 proteins is preferred.

The antibodies are then obtained from blood samples taken from the mammal. The techniques used to develop polyclonal antibodies are known in the art see, e.g., Methods of Enzymology, "Production of Antisera With Small Doses of Immunogen: Multiple Intradermal Injections", Langone, et al. eds. (Acad. Press, 1981)). Polyclonal antibodies produced by the animals can be further purified, for example, by binding to and elution from a matrix to which the peptide to which the antibodies were raised is bound. Those of skill in the art will know of various techniques common in the immunology arts for purification and/or concentration of polyclonal antibodies, as well as monoclonal antibodies, see, for example, Coligan, et al., Unit 9, Current Protocols in Immunology, Wiley Interscience, 1991).

Preferably, however, the YKL-40 antibodies produced will be monoclonal antibodies ("mAb's"). For preparation of monoclonal antibodies, immunization of a mouse or rat is preferred. The term "antibody" as used in this invention includes intact molecules as well as fragments thereof, such as, Fab and F(ab').sub.2, which are capable of binding an epitopic determinant. Also, in this context, the term "mAb's of the invention" refers to monoclonal antibodies with specificity for YKL-40.

The general method used for production of hybridomas secreting mAbs is well known (Kohler and Milstein, 1975). Briefly, as described by Kohler and Milstein the technique comprised isolating lymphocytes from regional draining lymph nodes of five separate cancer patients with either melanoma, teratocarcinoma or cancer of the cervix, glioma or lung, (where samples were obtained from surgical specimens), pooling the cells, and fusing the cells with SHFP-1. Hybridomas were screened for production of antibody which bound to cancer cell lines.

Confirmation of YKL-40 specificity among mAb's can be accomplished using relatively routine screening techniques (such as the enzyme-linked immunosorbent assay, or "ELISA") to determine the elementary reaction pattern of the mAb of interest. It is also possible to evaluate an mAb to determine whether it has the same specificity as a mAb of the invention without undue experimentation by determining whether the mAb being tested prevents a mAb of the invention from binding to YKL-40 isolated as described above, if the mAb being tested competes with the mAb of the invention, as shown by a decrease in binding by the mAb of the invention, then it is likely that the two monoclonal antibodies bind to the same or a closely related epitope. Still another way to determine whether a mAb has the specificity of a mAb of the invention is to pre-incubate the mAb of the invention with an antigen with which it is normally reactive, and determine if the mAb being tested is inhibited in its ability to bind the antigen. If the mAb being tested is inhibited then, in all likelihood, it has the same, or a closely related, epitopic specificity as the mAb of the invention.

Immunoassay Procedures

The immunoassay procedure used must be quantitative so that levels of YKL-40 in an individual with disease may be distinguished from normal levels which may be present in healthy humans and/or background levels measured in the individual. Competitive and sandwich assays on a solid phase using detectable labels (direct or indirect) are, therefore, preferred. The label will provide a detectable signal indicative of binding of antibody to the YKL-40 antigen. The antibody or antigen may be labeled with any label known in the art to provide a detectable signal, including radioisotopes, enzymes, fluorescent molecules, chemiluminescent molecules, bioluminescent molecules and colloidal gold. Of the known assay procedures, radioimmunoassay (RIA) or enzyme-linked immunoassay (ELISA) are most preferred for its sensitivity. A radioisotope will, therefore, be the preferred label.

Accordingly, in a specific embodiment of the method according to the present invention the YKL-40 level is determined using an immunoassay. In one version of this embodiment the immunoassay is a competitive immunoassay.

In one embodiment of the invention, the immunoassay uses a monoclonal antibody to measure YKL-40. In an alternative embodiment of the invention the immunoassay uses a polyclonal antibody to measure YKL-40.

When a method of the present invention utilizes an immunoassay, then a detectable label selected from the group consisting of radioisotopes, enzymes, fluorescent molecules, chemiluminescent molecules, bioluminescent molecules and colloidal metals, may be used to measure YKL-40.

Examples of metallic ions which can be directly bound to an antibody, or indirectly bound to the YKL-40 antigen are well-known to those of ordinary skill in the art and include $^{125}$I, $^{111}$In, $^{97}$Ru, $^{67}$Ga, $^{68}$Ga, $^{72}$As, $^{89}$Zr, $^{90}$Y and $^{201}$Tl. Preferred for its ease of attachment without compromise of antigen binding specificity is $^{125}$I (sodium salt, Amersham, United Kingdom). Labeling of YKL-40 with $^{125}$I may be performed according to the method described in Salacinski, et al. (1981). Iodogen for use to provide the $^{125}$I label (1,3,4,6-tetrachloro-3.alpha., 6.alpha.-diphenyl glycoluril) is commercially available from Pierce and Warriner, Chester, England.

In a specific preferred embodiment of the invention plasma levels of YKL-40 can be determined in duplicates by a two-site, sandwich-type enzyme-linked immunosorbent assay (ELISA) (such as e.g. the commercial Quidel, California, USA) (Harvey et al. 1998), using streptavidin-coated microplate wells, a biotinylated-Fab monoclonal capture antibody, and an alkaline phosphatase-labeled polyclonal detection antibody. When Quidel was used the recovery of the ELISA was 102% and the detection limit 10 µg/L. Sensitivity in this context is defined as the detectable mass equivalent to twice the standard deviation of the zero binding values. The standard curve will generally be linear between 20 and 300 µg/l. The intra-assay coefficients of variations were 5% (at 40 µg/L), 4% (at 104 µg/L), and 4% (at 155 µg/L). The interassay coefficient of variation was <6%.

In another embodiment of the invention a radioimmunoassay is used, wherein standards or samples are incubated with a substantially equal volume of YKL-40 antiserum and of YKL-40 tracer. Standards and samples are generally assayed in duplicate. The sensitivity (detection limit) of the assay of the invention is about 10 µg/l. Sensitivity in this context is defined as the detectable mass equivalent to twice the standard deviation of the zero binding values. The standard curve will generally be linear between 20 and 100 µg/l The intra- and interassay coefficients of variance for the assay described in the following examples are <6.5% and <12%, respectively.

It will be appreciated by those skilled in the art that, although not necessarily as sensitive as an RIA, assay procedures using labels other than radioisotopes have certain advantages and may, therefore, be employed as alternatives to a RIA format.

For example, an enzyme-linked immunosorbent assay (ELISA) may be readily automated using an ELISA microtiter plate reader and reagents which are readily available in many research and clinical laboratories. Fluorescent, chemiluminescent and bioluminescent labels have the advantage of being visually detectable, though they are not as useful as radioisotopes to quantify the amount of antigen bound by antibody in the assay.

PCR Based Assays

Further, it will be appreciated by those of skill in the art that means other than immunoassays may be employed to detect and quantify the presence of YKL-40 in a biological sample. For example, a polynucleotide encoding YKL-40 may be detected using quantitative polymerase chain reaction (PCR) protocols known in the art. Accordingly, in one embodiment of the method according to the present invention the YKL-40 level is determined in a PCR based assay. The preferred method for performance of quantitative PCR is a competitive PCR technique performed using a competitor template containing an induced mutation of one or more base pairs which results in the competitor differing in sequence or size from the target YKL-40 gene template. One of the primers is biotinylated or, preferably, aminated so that one strand (usually the antisense strand) of the resulting PCR product can be immobilized via an amino-carboxyl, amino-amino, biotin-streptavidin or other suitably tight bond to a solid phase support which has been tightly bound to an appropriate reactant. Most preferably, the bonds between the PCR product, solid phase support and reactant will be covalent ones, thus reliably rendering the bonds resistant to uncoupling under denaturing conditions.

Once the aminated or biotinylated strands of the PCR products are immobilized, the unbound complementary strands are separated in an alkaline denaturing wash and removed from the reaction environment. Sequence-specific oligonucleotides ("SSO's") corresponding to the target and competitor nucleic acids are labelled with a detection tag. The SSO's are then hybridized to the antisense strands in absence of competition from the removed unbound sense strands. Appropriate assay reagents are added and the degree of hybridization is measured by ELISA measurement means appropriate to the detection tag and solid phase support means used, preferably an ELISA microplate reader. The measured values are compared to derive target nucleic acid content, using a standard curve separately derived from PCR reactions amplifying templates including target and competitor templates. This method is advantageous in that it is quantitative, does not depend upon the number of PCR cycles, and is not influenced by competition between the SSO probe and the complementary strand in the PCR product.

Alternatively, part of the polymerization step and the entire hybridization step can be performed on a solid phase support. In this method, it is a nucleotide polymerization primer (preferably an oligonucleotide) which is captured onto a solid phase support rather than a strand of the PCR products. Target and competitor nucleic acid PCR products are then added in solution to the solid phase support and a polymerization step is performed. The unbound sense strands of the polymerization product are removed under the denaturing conditions described above.

A target to competitor nucleic acid ratio can be determined by detection of labeled oligonucleotide SSO probes using appropriate measurement means (preferably ELISA readers) and standard curve as described supra. The efficiency of this method can be so great that a chain reaction in the polymerization step may be unnecessary, thus shortening the time needed to perform the method. The accuracy of the method is also enhanced because the final polymerization products do not have to be transferred from a reaction tube to a solid phase support for hybridization, thus limiting the potential for their loss or damage. If necessary for a particular sample, however, the PCR may be used to amplify the target and competitor nucleic acids in a separate reaction tube, followed by a final polymerization performed on the solid phase support.

Molecules capable of providing different, detectable signals indicative of the formation of bound PCR products known to those skilled in the art (such as labeled nucleotide chromophores which will form different colors indicative of the formation of target and competitor PCR products) can be added to the reaction solution during the last few cycles of the reaction. The ratio between the target and competitor nucleic acids can also be determined by ELISA or other appropriate measurement means and reagents reactive with detection tags coupled to the 3' end of the immobilized hybridization primers. This method may also be adapted to detect whether a particular gene is present in the sample (without quantifying it) by performing a conventional noncompetitive PCR protocol.

Those of ordinary skill in the art will know, or may readily ascertain, how to select suitable primers for use in the above methods. For further details regarding the above-described techniques, reference may be made to the disclosures in Kohsaka, et al., Nuc. Acids Res., 21:3469-3472, 1993; Bunn, et al., U.S. Pat. No. 5,213,961; and to Innis, et al., PCR Protocols: A Guide to Methods and Applications, Acad. Press, 1990, the disclosures of which are incorporated herein solely for purposes of illustrating the state of the art regarding quantitative PCR protocols.

Reference Levels

An increased level of YKL-40 is indicative of the presence of a non-specific disease or disorder, and may therefore be used to diagnose the presence of such non-specific disease or disorder. Whether the YKL-40 level of a given subject is increased or not may be asserted by comparing a determined value with that of a reference level. The reference level may furthermore be one or more reference levels that for instance each reflects an increased severity of a non-specific disease or disorder, or the reference level may for instance be one or more reference levels obtained by previous measurements of samples from the same subject.

Previously, YKL-40 levels have been reported for e.g. various diseases or from healthy individuals, hereby giving an indication of the normal level. However, such previously reported "normal" YKL-40 levels from healthy individuals where not supported by a follow-up over time investigating whether the "healthy individuals" remained healthy over time. Accordingly, previously reported YKL-40 levels therefore included individuals who at the time of sampling potentially had unidentified diseases, and the reported YKL-40 levels therefore did not represent a true "normal level". Such previously reported YKL-40 levels obtained from e.g. healthy individuals have also been reported as e.g. average levels without considering the effect of age.

As can be seen from the examples included in the present invention, the present inventors have identified a way to express a true "normal level". This normal level has been identified on the basis of a large population of healthy individuals, and the individuals have been followed over time to confirm whether they were true "healthy individuals". The inventors have surprisingly found that the identified "normal level" can be used to diagnose the presence of diseases or disorders, e.g. a non-specific disease or disorder, in a subject in accordance with the methods of the present invention. The present inventors have furthermore found that age has a great influence on the YKL-40 level, and that this is to be considered when utilizing the methods of the present invention.

A reference level for YKL-40 can be expressed in various ways; traditionally reference levels may be from a group of healthy individuals of various ages. The present inventors have investigated the influence of age on the YKL-40 level and found that a measured YKL-40 level preferably is compared with age specific group.

An age specific group of individuals may comprise individuals that are all born within the same year or decade or any other groupings such as groups comprising individuals that are of 0 to 10 years of age, 10 to 20 years of age, 20 to 30 years of age, 30 to 40 years of age, 40 to 50 years of age, 50 to 60 years of age, 60 to 70 years of age, 70 to 80 years of age, 80 to 90 years of age, 90 to 100 years of age, and so on. The intervals may span 2 years of age difference, 3, 4, or 5 years of age difference, 6, 7, 8, 9, 10 years of age difference (as written), 12, 15, 20 or more years of age difference. The intervals may furthermore be open ended e.g. the individuals are all above the age of 20, 30, 40, 50, 60 or other.

The present inventors have found that there is no statistically difference between the plasma YKL-40 level in men and in women (see example 1 herein). Accordingly, the group of individuals who form the basis for the calculation of the reference level may be a group of individuals of mixed sex or same sex. Reference levels may also be obtained from the same individual as is presently to be diagnosed for the presence of a disease or a disorder. For example may YKL-40 levels be measured in one or more samples obtained prior to diagnosis of the disease or disorder (pre-illness) and or prior to the establishment of symptoms of the disease or disorder (pre-symptom).

In a preferred embodiment of the invention, the reference level of YKL-40 is an average level obtained by measuring the YKL-40 levels in samples from healthy individuals, and more preferably the thereby obtained average level is an age adjusted average level.

Specifically, in one embodiment of the invention, the average level is an YKL-40 plasma level in a range from about 14 to about 168 µg/L (2.5%-97.5% percentile range), preferably a plasma level of less than about 124 µg/L (95% percentile), and more preferably a plasma level of less than 92 µg/L (90% percentile). Preferably, the average level is an YKL-40 plasma level in a range from about 35 to about 55 µg/l, such as preferably from about 40 to about 50 µg/l. In an even more specific embodiment of the invention the median level is an YKL-40 plasma level of about 42 µg/l. Plasma YKL-40 levels increase in both sexes with increasing age and there is no difference between plasma YKL-40 in women and men. These plasma YKL-40 levels have been found from samples of and by studying a large group of healthy subjects, hereby giving a well founded reference level for plasma YKL-40 levels that may be used in the method according to the present invention (see example 1 herein).

When the present invention utilizes an age-adjusted average level, then the average level may be age adjusted by adding 0.5 µg/l per year for women, and 0.8 µg/l per year for men. This age-adjustment is preferably performed for a previously measured YKL-40 level from the same subject, as may for example be relevant for the third and the fourth aspect of the invention. Alternatively, the reference level may be a set of YKL-40 age dependent reference levels, e.g. one or more reference levels of YKL-40, obtained by measuring the YKL-40 levels in samples from age distributed subpopulations of healthy individuals, i.e. age specific groups of individuals as described herein above, such as e.g. individuals that are all born within the same decade. For example a set of reference levels, each being the average YKL-40 plasma level for a group of healthy individuals within the following age groups: from 30 to 39 years, from 40 to 49 years, from 50 to 59 years, and from 60 to 69 years. Preferred sets of YKL-40 age dependent reference levels are given herein further below.

In a specific embodiment of the methods according to the invention, one of the one or more reference levels of YKL-40 is an age adjusted cut-off value corresponding to the $75^{th}$ percentile of YKL-40 as determined in healthy individuals.

In another specific embodiment of the methods according to the invention, one of the one or more reference levels of YKL-40 is an age adjusted cut-off value corresponding to the $85^{th}$ percentile of YKL-40 as determined in healthy individuals.

In another specific embodiment of the methods according to the invention, one of the one or more reference levels of YKL-40 is an age adjusted cut-off value corresponding to the $90^{th}$ percentile of YKL-40 as determined in healthy individuals.

In another specific embodiment of the methods according to the invention, one of the one or more reference levels of YKL-40 is an age adjusted cut-off value corresponding to the $95^{th}$ percentile of YKL-40 as determined in healthy individuals.

In another specific embodiment of the methods according to the invention, one of the one or more reference levels of YKL-40 is an age adjusted cut-off value corresponding to the $97.5^{th}$ percentile of YKL-40 as determined in healthy individuals.

In a preferred embodiment of the methods according to the invention the one or more reference levels of YKL-40 comprises a set of reference levels of YKL-40 obtained by measuring the YKL-40 levels in samples from healthy individuals: a first reference level being the median value of YKL-40, a second reference level being the $75^{th}$ percentile of YKL-40, a third reference level being the $85^{th}$ percentile of YKL-40, a fourth reference level being the $90^{th}$ percentile of YKL-40, a fifth reference level being the $95^{th}$ percentile of YKL-40, a sixth reference level being the $97.5^{th}$ percentile of YKL-40 in healthy individuals, a seventh reference level being a factor 4.5 of the median value of YKL-40, and a eighth reference level being a factor 5 of the median value of YKL-40 in healthy individuals.

Another way of specifying a reference level is by the use of a cut-off value. A cut-off value is a value that typically divides a number of individuals into two groups: those that have an YKL-40 level above a specific cut-off value, and those that have an YKL-40 level below the specified cut-off value. The cut-off value may be any value that represents a physiological YKL-40 level as measured in any type of biological sample, or as chosen by a person skilled in the art.

The cut-off value may be used as a yes or no indicator of whether an individual is within a certain category, in relation to the present invention this corresponds to the presence of a non-specific disease or to different stages of severity of a non-specific disease or disorder (as in relation to the fourth aspect of the invention).

In one embodiment of the invention the reference level of YKL-40 is an age adjusted cut-off value, such as e.g. a cut-off value of about 80 µg/l serum YKL-40, such as e.g. about 90 µg/l serum, about 100 µg/l serum, about 110 µg/l serum, about 120 µg/l serum, or about 130 µg/l serum YKL-40. Preferably about 100 µg/l serum YKL-40. The age adjustment may be performed as described herein elsewhere.

Accordingly, in a preferred embodiment of the invention, the reference level of YKL-40 is an age adjusted cut-off value corresponding to the $90^{th}$ percentile of plasma YKL-40 in healthy individuals, such as for example a YKL-40 plasma value of 92 µg/l for a subject of about 50 years of age, or a YKL-40 plasma value of 111 µg/l for a subject of about 60 years of age; and more preferably it is an age adjusted cut-off value corresponding to the $95^{th}$ percentile of plasma YKL-40 in healthy individuals, such as for example a YKL-40 plasma value of 100 µg/l for a subject of about 50 years of age, or a YKL-40 plasma value of 124 µg/l for a subject of about 60 years of age. When the $95^{th}$ percentile plasma level is age adjusted and applied as a cut-off value, there is allowed for greater potential individual variations in the YKL-40 level. The use of the $95^{th}$ percentile, or even the $97.5^{th}$ percentile, may for instance be relevant when the methods of the invention is used with focus on one individual subject. However, in some instances of the method of the present invention it is preferred that the $90^{th}$ percentile plasma YKL-40 level is applied. This is e.g. when the method is applied for screening purposes to identify non-specific diseases that have not yet given cause to symptoms. In the same manner, for e.g. screening purposes, it may furthermore be relevant to utilize the $70^{th}$ percentile, the $75^{th}$ percentile, or the $85^{th}$ percentile of the plasma YKL-40 level in healthy individuals, which percentile is used will depend on which level of sensitivity is desired. The lower the percentile selected, as e.g. a cut-off value, the higher sensitivity is obtained. By using a low percentile subjects may be found that yet only are slightly affected by a disease or disorder, such as e.g. in an early stage of a disease or disorder. However, the lower the percentile selected the higher is the fraction of subjects that may be found in the screening without actually having a non-specific disease or disorder, which may be due to the potential individual biological variations.

Accordingly, by determining whether the determined level of YKL-40 in the sample is above one or more of the reference levels provides furthermore the classification of the severity of the non-specific disease or disorder in the fourth aspect of the invention. In other words, the classification of the non-specific disease or disorder is provided by comparing the determined YKL-40 level from the sample with the one or more reference levels of YKL-40, wherein the higher the level of YKL-40 the more severe the non-specific disease or disorder is classified as.

The cut-off value may alternatively be defined as a plasma YKL-40 level corresponding to the following percentiles defined in 3610 healthy subjects:
the 70% percentile (defined as ln(plasma YKL-40)=3.1+ 0.02×age (years)),
the 75% percentile (defined as ln(plasma YKL-40)=3.2+ 0.02×age (years)),
the 90% percentile (defined as ln(plasma YKL-40)=3.5+ 0.02×age (years)); and
the 95% percentile (defined as ln(plasma YKL-40)=3.6+ 0.02×age (years)) according to age.

The cut-off value may furthermore be defined as a plasma YKL-40 level corresponding to the following percentiles defined in 3610 healthy subjects:

the 70% percentile (defined as ln(plasma YKL-40)=3.1+0.02×age (years)),
the 75% percentile (defined as ln(plasma YKL-40)=3.2+0.02×age (years)),
the 85% percentile (defined as ln(plasma YKL-40)=3.4+0.02×age (years)),
the 90% percentile (defined as ln(plasma YKL-40)=3.5+0.02×age (years)),
the 95% percentile (defined as ln(plasma YKL-40)=3.6+0.02×age (years)), and
the 97.5% percentile (defined as ln(plasma YKL-40)=3.9+0.02×age (years)), according to age.

Figure 3A:
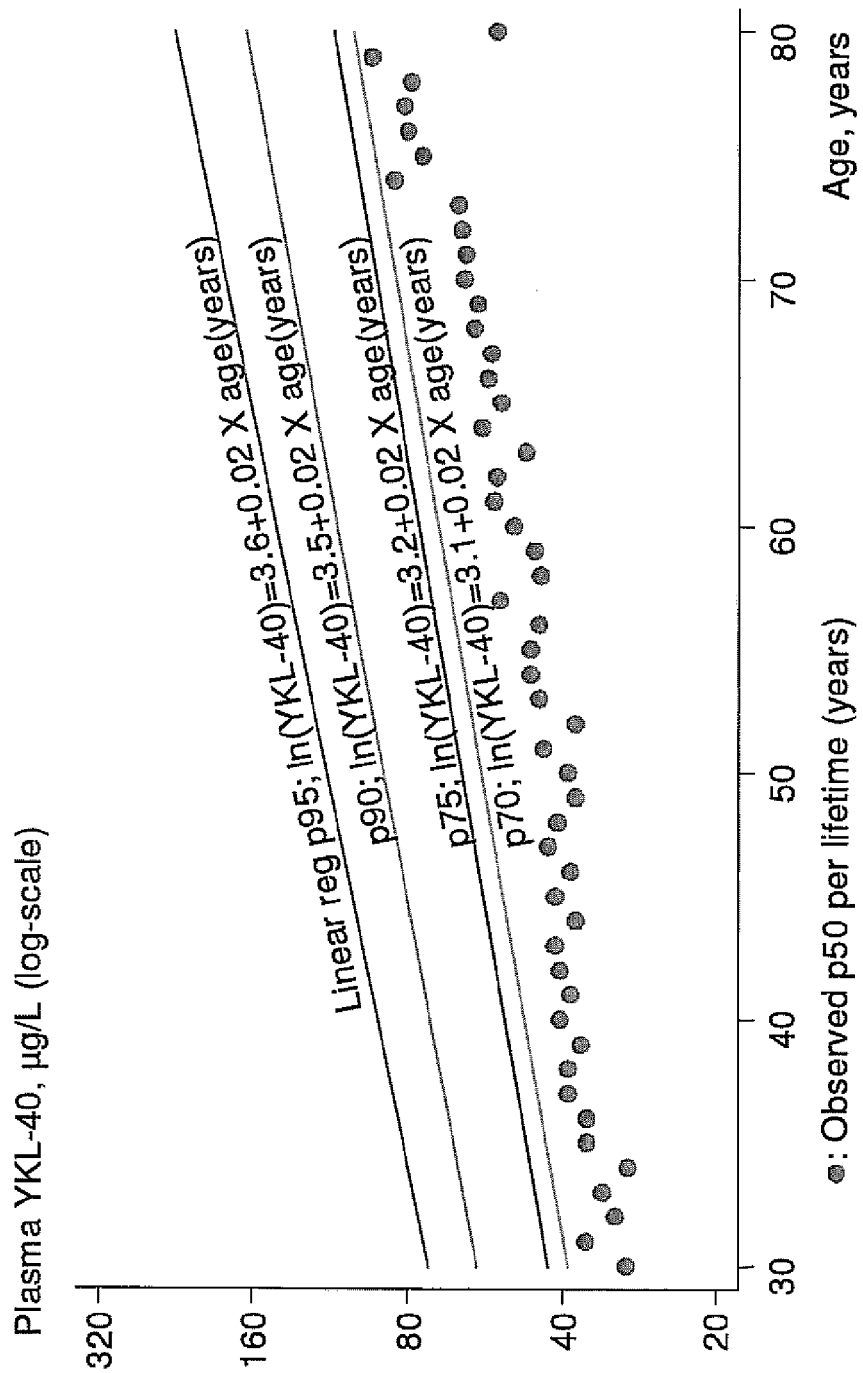
FIG. 3A. Plasma concentrations of YKL-40 were determined in 2116 healthy women and 1494 healthy men. The participants had no known disease at the time of blood sampling in 1991-1994 and remained healthy during the 16 years follow-up period (i.e. none were dead or had develop cancer, ischaemic cardiovascular disease, liver disease, diabetes, chronic obstructive pulmonary disease, asthma, rheumatoid arthritis, inflammatory bowel disease, and pneumonia). The figure illustrates the 50% percentile plasma YKL-40 in these healthy participants (circles), the 70% percentile (defined as ln(plasma YKL-40)=3.1+0.02×age (years)), the 75% percentile (defined as ln(plasma YKL-40)=3.2+0.02×age (years)), the 90 percentile (defined as ln(plasma YKL-40)=3.5+0.02×age (years)) and the 95% percentile (defined as ln(plasma YKL-40)=3.6+0.02×age (years)) according to age. Women and men were combined.
Figure 3B:
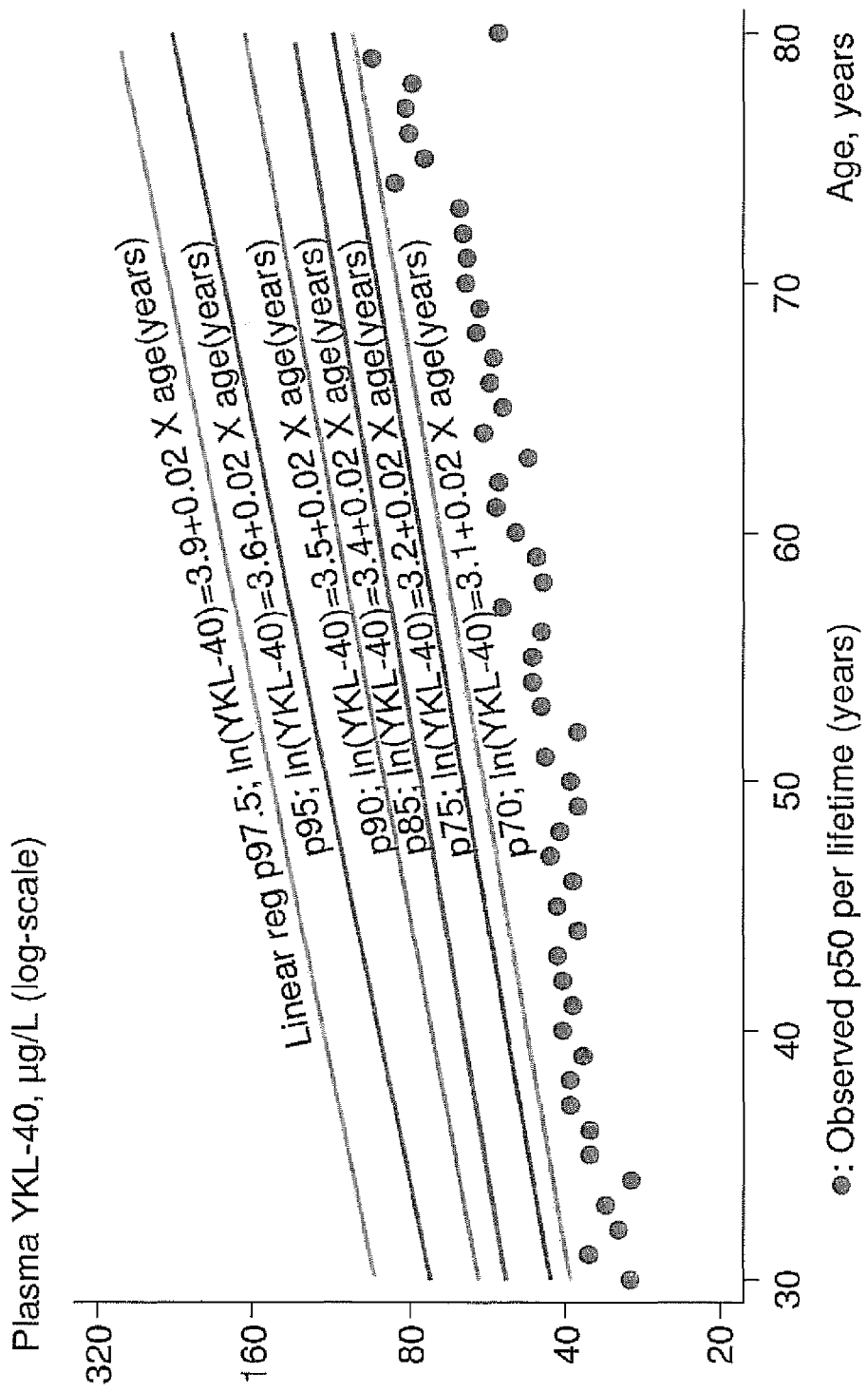
FIG. 3B. Corresponds to FIG. 3A, with additional percentiles for plasma YKL-40: the 85% percentile (defined as ln(plasma YKL-40)=3.4+0.02×age (years)), and the 97.5% percentile (defined as ln(plasma YKL-40)=3.9+0.02×age (years)).

In a preferred embodiment of the methods according to the present invention the reference level of YKL-40 is calculated according to the immediately above mentioned formulas, by the use of the age of the subject. The formulas are furthermore depicted in FIG. 3A and FIG. 3B, which figures may be used in a more direct approach allowing for the determination of a cut-off value without the need for calculations. FIGS. 3A and 3B furthermore allows for an immediate comparison of a measured YKL-40 level and the subject age with e.g. both the $90^{th}$ percentile and the $95^{th}$ percentile. Hereby furthermore giving an immediate indication of the extend to which a measured YKL-40 level differs from the reference levels. By use of the above-mentioned formula for the $90^{th}$ percentile, the cut of value for subjects having an age of about 20 years, about 30 years, about 40 years, about 50 years, about 60 years, and about 70 years are: about 49 µg/l, about 60 µg/l, about 74 µg/l, about 90 µg/l, about 110 µg/l, and about 134 µg/l YKL-40, respectively. Correspondingly, the above mentioned formula for the $95^{th}$ percentile give the following cut-off values: about 55 µg/l, about 67 µg/l, about 81 µg/l, about 99 µg/l, about 122 µg/l, and about 148 µg/l YKL-40, respectively.

In one embodiment of the methods according to the invention the reference level of YKL-40 is an age adjusted cut-off value corresponding to the $70^{th}$ percentile of serum or plasma YKL-40 levels in healthy individuals. More preferably the age adjusted cut-off value is the $70^{th}$ percentile defined as: ln(plasma YKL-40)=3.1+0.02×age (years).

In another embodiment of the methods according to the invention the reference level of YKL-40 is an age adjusted cut-off value corresponding to the $75^{th}$ percentile of serum or plasma YKL-40 levels in healthy individuals. More preferably the age adjusted cut-off value is the $75^{th}$ percentile defined as: ln(plasma YKL-40)=3.2+0.02×age (years).

In another embodiment of the methods according to the invention the reference level of YKL-40 is an age adjusted cut-off value corresponding to the $85^{th}$ percentile of serum or plasma YKL-40 levels in healthy individuals. More preferably the age adjusted cut-off value is the $85^{th}$ percentile defined as: ln(plasma YKL-40)=3.4+0.02×age (years).

In another embodiment of the methods according to the invention the reference level of YKL-40 is an age adjusted cut-off value corresponding to the $90^{th}$ percentile of serum or plasma YKL-40 levels in healthy individuals. More preferably the age adjusted cut-off value is the $90^{th}$ percentile defined as: ln(plasma YKL-40)=3.5+0.02×age (years).

In another embodiment of the methods according to the invention the reference level of YKL-40 is an age adjusted cut-off value corresponding to the $95^{th}$ percentile of serum or plasma YKL-40 levels in healthy individuals. More preferably the age adjusted cut-off value is the $95^{th}$ percentile defined as: ln(plasma YKL-40)=3.6+0.02×age (years).

In another embodiment of the methods according to the invention the reference level of YKL-40 is an age adjusted cut-off value corresponding to the $97.5^{th}$ percentile of serum or plasma YKL-40 levels in healthy individuals. More preferably the age adjusted cut-off value is the $97.5^{th}$ percentile defined as: ln(plasma YKL-40)=3.9+0.02×age (years).

In a specific embodiment of the methods according to the invention the reference level of YKL-40 is a set of YKL-40 age dependent cut-off values defined as two or more of the herein immediately above mentioned age adjusted cut-off value corresponding to the $70^{th}$, $75^{th}$, $85^{th}$, $90^{th}$, $95^{th}$, or $97.5^{th}$ percentile, respectively.

In another preferred embodiment of the first or fourth aspect of the invention, the reference level of YKL-40 is a set of YKL-40 age dependent cut-off values defined by two or more of the percentiles $70^{th}$, $75^{th}$, $85^{th}$, $90^{th}$, $95^{th}$ and $97.5^{th}$, as e.g. preferably calculated by the above mentioned formulas. A set of YKL-40 age dependent cut-off values may furthermore be calculated for a set of age groups, e.g. 20-29 years, 30-39 years, 40-49 years etc. where for instance the cut-off value is the highest value in the age group. In one preferred embodiment of the first or fourth aspect of the invention the set of cut-off values is as follows:

| Age intervals (years) | Age dependent cut-off values for healthy subjects | | | | |
| --- | --- | --- | --- | --- | --- |
| | $70^{th}$ percentile (µg/l YKL-40) | $75^{th}$ percentile (µg/l YKL-40) | $85^{th}$ percentile (µg/l YKL-40) | $90^{th}$ percentile (µg/l YKL-40) | $95^{th}$ percentile (µg/l YKL-40) |
| 20-29 | 40 | 44 | 54 | 59 | 65 |
| 30-39 | 48 | 54 | 65 | 72 | 80 |
| 40-49 | 59 | 65 | 80 | 88 | 98 |
| 50-59 | 72 | 80 | 98 | 108 | 119 |
| 60-69 | 88 | 98 | 119 | 132 | 145 |
| 70-79 | 108 | 119 | 154 | 161 | 178 |
| 80-89 | 132 | 145 | 178 | 196 | 217 |

In another embodiment of the methods according to the invention the reference level of YKL-40 is an age adjusted cut-off value corresponding to the $75^{th}$ percentile of serum or Likewise obtained by the above mentioned formulas is a more detailed set of preferred age dependent cut-off values to be used in the methods according to the present invention:

| Age dependent cut-off values for healthy subjects | | | | | |
|---|---|---|---|---|---|
| Age intervals (years) | 70th percentile (μg/l YKL-40) | 75th percentile (μg/l YKL-40) | 85th percentile (μg/l YKL-40) | 90th percentile (μg/l YKL-40) | 95th percentile (μg/l YKL-40) |
| 20-24 | 36 | 40 | 48 | 54 | 59 |
| 25-29 | 40 | 44 | 54 | 59 | 65 |
| 30-34 | 44 | 48 | 59 | 65 | 72 |
| 35-39 | 48 | 54 | 65 | 72 | 80 |
| 40-44 | 54 | 59 | 72 | 80 | 88 |
| 45-49 | 59 | 65 | 80 | 88 | 98 |
| 50-54 | 65 | 72 | 88 | 98 | 108 |
| 54-59 | 72 | 80 | 98 | 108 | 119 |
| 60-64 | 80 | 88 | 108 | 119 | 132 |
| 65-69 | 88 | 98 | 119 | 132 | 145 |
| 70-74 | 98 | 108 | 132 | 145 | 161 |
| 75-79 | 108 | 119 | 145 | 161 | 178 |
| 80-84 | 119 | 132 | 161 | 178 | 196 |
| 85-89 | 132 | 145 | 178 | 196 | 217 |

As described above a set of YKL-40 age dependent reference levels can be used in the methods according to the present invention. A preferred set of age dependent reference levels for healthy subjects can be calculated by the above formulas. Accordingly, a set of preferred age dependent reference levels to be used in the methods according to the present invention are as follows:

| Age dependent reference levels for healthy subjects | | | | | |
|---|---|---|---|---|---|
| Age intervals (years) | 70th percentile (μg/l YKL-40) | 75th percentile (μg/l YKL-40) | 85th percentile (μg/l YKL-40) | 90th percentile (μg/l YKL-40) | 95th percentile (μg/l YKL-40) |
| 20-29 | 33-40 | 37-44 | 45-54 | 49-59 | 55-65 |
| 30-39 | 40-48 | 45-54 | 55-65 | 60-72 | 67-80 |
| 40-49 | 49-59 | 55-65 | 67-80 | 74-88 | 81-98 |
| 50-59 | 60-72 | 67-80 | 81-98 | 90-108 | 99-119 |
| 60-69 | 74-88 | 81-98 | 99-119 | 110-132 | 122-145 |
| 70-79 | 90-108 | 99-119 | 122-154 | 134-161 | 148-178 |
| 80-89 | 110-132 | 122-145 | 148-178 | 164-196 | 181-217 |

Likewise obtained by the above mentioned formulas is a more detailed set of preferred age dependent reference levels to be used in the methods according to the present:

| Age dependent reference levels for healthy subjects | | | | | |
|---|---|---|---|---|---|
| Age intervals (years) | 70th percentile (μg/l YKL-40) | 75th percentile (μg/l YKL-40) | 85th percentile (μg/l YKL-40) | 90th percentile (μg/l YKL-40) | 95th percentile (μg/l YKL-40) |
| 20-24 | 33-36 | 37-40 | 45-48 | 49-54 | 55-59 |
| 25-29 | 37-40 | 40-44 | 49-54 | 55-59 | 60-65 |
| 30-34 | 40-44 | 45-48 | 55-59 | 60-65 | 67-72 |
| 35-39 | 45-48 | 49-54 | 60-65 | 67-72 | 74-80 |
| 40-44 | 49-54 | 55-59 | 67-72 | 74-80 | 81-88 |
| 45-49 | 55-59 | 60-65 | 74-80 | 81-88 | 90-98 |
| 50-54 | 60-65 | 67-72 | 81-88 | 90-98 | 99-108 |
| 54-59 | 67-72 | 74-80 | 90-98 | 99-108 | 110-119 |
| 60-64 | 74-80 | 81-88 | 99-108 | 110-119 | 122-132 |
| 65-69 | 81-88 | 90-98 | 110-119 | 122-132 | 134-145 |
| 70-74 | 90-98 | 99-108 | 122-132 | 134-145 | 148-161 |
| 75-79 | 99-108 | 110-119 | 134-145 | 148-161 | 164-178 |
| 80-84 | 110-119 | 122-132 | 148-161 | 164-178 | 181-196 |
| 85-89 | 122-132 | 134-145 | 164-178 | 181-196 | 200-217 |

In yet another embodiment of the invention, the determined level of YKL-40 in the sample is said to be above the reference level and thereby indicating the presence of a non-specific disease or disorder when the level of YKL-40 in the sample is increased by about 25% or more, such as e.g. by about 50% or more, about 60% or more, about 70% or more, about 80% or more, about 90% or more, about 100% or more, about 110% or more, about 120% or more, about 130% or more, or about 150% or more.

As previously described herein for the third and for the fourth aspect of the invention, the reference level may alternatively be obtained from the same subject at a previous point in time. Accordingly, in the third aspect of the invention the method is a method for diagnosing the presence of a non-specific disease or disorder in a subject, said method comprising
  i) determining the level of YKL-40 in a sample obtained from the subject; and
  ii) comparing said level of YKL-40 with a reference level of YKL-40, said reference level being a previously determined level of YKL-40 from the same subject;
wherein a level of YKL-40 in the sample increased to a factor of 1.10 compared to the reference level of YKL-40 indicates the presence of a non-specific disease or disorder. Preferably, the reference level of YKL-40 is, if necessary, an age adjusted reference level, for example obtained by adding 0.5 µg/l per year for women, and 0.8 µg/l per year for men. This may for instance be relevant when the previously obtained reference level is more than 3 years old, such as e.g. more than 5 years old, more than 8 years old, or more than 10 years old. For example when the previously obtained reference level is more than 10 years old.

When the applied reference level is a previously determined level of YKL-40 from the same subject, the determined level of YKL-40 in the sample is said to be significantly above the reference level and thereby significantly indicating the presence of a non-specific disease or disorder when the level of YKL-40 in the sample is increased by about 109% or more. The following is a calculation example, where the previously measured YKL-40 level is 50 µg/l, and an YKL-40 level increased by 109% is calculated: 50 µg/l+(50×1.09) µg/l=50 µg/l+54.5 µg/l=104.5 µg/l. In an increase by about 109% or more is included any method variation, biological variation or other that may influence the YKL-40 level, see example 2 herein for details.

As mentioned herein above the present inventors have found the mean increase of the YKL-40 level to be 0.5 µg/l per year for women, and 0.8 µg/l per year for men. Accordingly, if a previously determined level of YKL-40 from the same subject increases by more than this, then there is a risk that a non-specific disease or disorder is present, or e.g. that an existing non-specific disease or disorder yet to be identified is getting more severe. Therefore an increase, but an increase by less than the above described 109%, may be indicative for the presence of a disease or disorder, or indicative for the worsening of a disease or disorder. Accordingly, if for instance a previously determined YKL-40 level was about 60 µg/l for a woman of about 25 years of age, and a new level was determined 5 years after, the increase due to age should be about 2.5 µg/l, i.e. a new age corrected value should be about 62.5 µg/l. If this value instead was measured to about 66 µg/l, it would give an indication that a non-specific disease or disorder may be present.

In a specially preferred embodiment of the method according to the present invention, where the reference level is obtained as a previous measurement from the same individual, a level of YKL-40 in the sample increased to a factor of 1.10 compared to the reference level of YKL-40 indicates the presence of a non-specific disease or disorder, more preferably at least a factor of 1.25, such as e.g. a factor of 1.30, or a factor of 1.40; even more preferably at least a factor of 1.50, such as e.g. a factor of 1.60, a factor of 1.70, or a factor of 1.75; yet even more preferably at least a factor of 1.75, such as e.g. a factor of 1.80, or a factor of 1.90, or a factor of 2; most preferably at least a factor of 2, such as e.g. a factor of 2.10, a factor of 2.20, a factor of 2.25, or a factor of 2.50 compared to the reference level of YKL-40 indicates the presence of a non-specific disease or disorder. The following is a calculation example giving a level being increased to a factor of 1.10 compared to a reference level of 50 µg/l: 50 µg/l×1.10=55 µg/l (i.e. The new level is: 55 µg/l).

It follows from the above that the higher the increase the stronger is the indication that a non-specific disease or disorder is present. In a preferred embodiment of the third aspect of the invention a level of YKL-40 in the sample increased to a factor of 2, such as at least a factor of 2, compared to the reference level of YKL-40 obtained as a previous measurement from the same individual, indicates the presence of a non-specific disease or disorder. An increase to at least a factor of 2 corresponds to the above-mentioned significant increase by 109% or more.

If for instance a previously determined level of YKL-40 from the same subject already was at a level where a non-specific disease or disorder is to be expected to be present, see the first aspect of the present invention, then an increase over time is not expected to be more than the age dependent increase of 0.5 µg/l per year for women or 0.8 µg/l per year for men; unless the non-specific disease or disorder is worsening. In this case it is especially preferred that the factor describing an increase is low. Accordingly, preferably that a level of YKL-40 in the sample increased by at least a factor of 1.10 compared to the reference level of YKL-40 indicates the presence of a non-specific disease or disorder, or a worsening of the non-specific disease or disorder.

Furthermore, in one embodiment of the method according to the present invention, where the reference level is obtained as a previous measurement from the same individual, a level of YKL-40 in the sample decreased to a factor of 0.90 compared to a reference level indicates that a changes to the better has occurred. Accordingly, in one embodiment wherein a level of YKL-40 in the sample being decreased at least to a factor of 0.90 compared to the YKL-40 reference level indicates that a non-specific disease or disorder has evolved to a less severe stage of the disease or disorder, or even that the subject has been cured, more preferably decreased at least to a factor of 0.80, such as e.g. a factor of 0.70; even more preferably decreased at least to a factor of 0.60; yet even more preferably decreased at least to a factor of 0.50; most preferably decreased at least to a factor of 0.48, such as e.g. a factor of 0.45, a factor of 0.43, a factor of 0.40, or a factor of 0.38, compared to the YKL-40 reference level. The following is a calculation example giving a level being decreased to a factor of 0.90 compared to a reference level of 100 µg/l: 100 µg/l×0.90=90 µg/l, i.e. the new and lower plasma YKL-40 level is 90 µg/l. When it is written that a level is decreased at least to a factor of e.g. 0.90, it is intended to mean that the level is decreased to a factor 0.90 or e.g. 0.80, 0.70 etc., i.e., that a level of 100 µg/l is decreased to at least 90 µg/l or a lower value.

In a more preferred embodiment of the third aspect of the invention a level of YKL-40 in the sample being decreased by 52% compared to the YKL-40 reference level indicates that a non-specific disease or disorder has evolved to a less severe stage of the disease or disorder. The following is a calculation example, where the previously measured YKL-40 level is 100 µg/l, and an YKL-40 level decreased by 52% is calculated: 100 µg/l−(100×0.52) µg/l=100 µg/l−52 µg/l=48 µg/l. In a decrease by about 52% is included any method variation, biological variation or other that may influence the YKL-40 level, see example 2 herein for details.

In relation to the fourth aspect of the invention it is especially preferred to classifying the severity of a non-specific disease or disorder by determining the increase in the YKL-40 level of the sample compared to the one or more reference levels. Accordingly, in one embodiment a level of YKL-40 in the sample being increased to at least a factor of 1.10 or more compared to the YKL-40 reference level indicates that a non-specific disease or disorder has evolved to a more severe stage of the disease or disorder, more preferably increased to at least a factor of 1.25, such as e.g. a factor of 1.30, or a factor of 1.40; even more preferably increased to at least a factor of 1.50, such as e.g. a factor of 1.60, a factor of 1.70, or a factor of 1.75; yet even more preferably increased to at least a factor of 1.75, such as e.g. a factor of 1.80, or a factor of 1.90, or a factor of 2; most preferably increased to at least a factor of 2, such as e.g. a factor of 2.10, a factor of 2.20, a factor of 2.25, or a factor of 2.50 compared to the YKL-40 reference level indicates that a non-specific disease or disorder have evolved to a more severe stage of the disease or disorder. The use of these factors for determining an increase is further described above for the remaining aspects of the present invention.

In a more preferred embodiment of the fourth aspect of the invention a level of YKL-40 in the sample being increased by 109% compared to the YKL-40 reference level indicates that a non-specific disease or disorder have evolved to a more severe stage of the disease or disorder. The following is a calculation example, where the previously measured YKL-40 level is 50 µg/l, and an YKL-40 level increased by 109% is calculated: 50 µg/l+(50×1.09) µg/l=50 µg/l+54.5 µg/l=104.5 µg/l.

Likewise the classification of the severity of a non-specific disease or disorder according to the fourth aspect of the present invention may be performed by determining a decrease in the YKL-40 level of the sample compared to the one or more reference levels. Accordingly, in one embodiment wherein a level of YKL-40 in the sample being decreased at least to a factor of 0.90 compared to the YKL-40 reference level indicates that a non-specific disease or disorder have evolved to a less severe stage of the disease or disorder, more preferably decreased to least by a factor of 0.80, such as e.g. a factor of 0.70; even more preferably decreased at least to a factor of 0.60; yet even more preferably decreased at least to a factor of 0.50; most preferably decreased at least to a factor of 0.48, such as e.g. a factor of 0.45, a factor of 0.43, a factor of 0.40, or a factor of 0.38, compared to the YKL-40 reference level indicates that a non-specific disease or disorder have evolved to a less severe stage of the disease or disorder. The use of these factors for determining an increase is further described above for the remaining aspects of the present invention.

In a more preferred embodiment of the fourth aspect of the invention a level of YKL-40 in the sample being decreased by 52% compared to the YKL-40 reference level indicates that a non-specific disease or disorder have evolved to a less severe stage of the disease or disorder.

A preferred embodiment of the fourth aspect of the invention relates to a method for classifying the severity of a non-specific disease or disorder in a subject, said method comprising
i) determining the level of YKL-40 in a sample obtained from the subject; and
ii) comparing the level of YKL-40 with one or more reference levels of YKL-40, said reference levels being one or more previously determined levels of YKL-40 from the same subject;
wherein a level of YKL-40 in the sample being increased to at least a factor 1.10 compared to the reference level of YKL-40 indicates that the disease or disorder has evolved to a more severe stage of the disease or disorder; and
wherein a level of YKL-40 in the sample being decreased to at least a factor 0.90 compared to the reference level of YKL-40 indicates that the disease or disorder has evolved to a less severe stage of the disease or disorder.

It follows from the above that the higher the increase the more severe a stage the disease or disorder has evolved to. In a preferred embodiment of the fourth aspect of the invention a level of YKL-40 in the sample increased to a factor of 2, such as at least a factor of 2, compared to the reference level of YKL-40 obtained as a previous measurement from the same individual, indicates that the disease or disorder have evolved to a more severe stage of the disease or disorder Other Biomarkers YKL-40 is an independent general biomarker for the presence of non-specific disease or for classifying the severity of a non-specific diseases or disorder and may be used accordingly. However, YKL-40 may also be used in combination with other known biomarkers such as C-reactive protein (CRP), ESR, carcinoembryonic antigen (CEA), CA-125, human epidermal growth factor receptor 2 (HER2), CA19-9, lactate dehydrogenase (LDH), tissue inhibitor metallo proteinase 1 (TIMP-1), brain natriuretic protein (BNP), interleukins, tumor necrosis factor-alfa, homocysteine, amyloid A protein, Pregnancy-Associated Plasma Protein-A, troponines, soluble intercellular adhesion molecule-1, soluble UPAR, the aminoterminal propeptide of type III procollagen (P-III-NP), monocyte chemoattractant protein-1, fibrin D-dimer, Growth-differentiation factor-15, Ischemia-modified albumin, lipoprotein-associated phospholipase A2, matrix metalloproteinases, pentraxin 3, secretory phospholipase A2 group IIA, intercellular adhesion molecule-1, Heart-type fatty acid-binding protein (H-FABP), Myosin light chain-1 (MLC-1), P-selectin and CKMB. Of the mentioned biomarkers, both the soluble and insoluble forms of the proteins are of relevance for the present invention, such as UPAR and soluble UPAR; intercellular adhesion molecule-1 and soluble intercellular adhesion molecule-1 and others. The levels of any of the abovementioned markers may be measured in a biological sample such as a blood, serum, plasma or tissue sample and by any means available such as by use of immunoassays or PCR based assays or several assay types in combination.

It is thus furthermore an aspect of the present invention to provide means for diagnosing subjects according to their YKL-40 levels in combination with levels of other biomarkers these being selected from the non-limiting group consisting of C-reactive protein (CRP), ESR, carcinoembryonic antigen (CEA), CA-125, human epidermal growth factor receptor 2 (HER2), CA19-9, lactate dehydrogenase (LDH), tissue inhibitor metallo proteinase 1 (TIMP-1), brain natriuretic protein (BNP), interleukins and tumor necrosis factor-alfa, homocysteine, amyloid A protein, Pregnancy-Associated Plasma Protein-A, troponines, soluble intercellular adhesion molecule-1, soluble UPAR, the aminoterminal propeptide of type III procollagen (P-III-NP), monocyte chemoattractant protein-1, fibrin D-dimer, Growth-differentiation factor-15, Ischemia-modified albumin, lipoprotein-associated phospholipase A2, matrix metalloproteinases and CKMB; preferably C-reactive protein, ESR, carcinoembryonic antigen (CEA), CA-125, human epidermal growth factor receptor 2 (HER2), CA19-9, lactate dehydrogenase (LDH), brain natriuretic protein, interleukins, tumor necrosis factor-alfa, homocystein, amyloid A protein, Pregnancy-Associated Plasma Protein-A, troponines, soluble intercellular adhesion molecule-1, soluble UPAR, the aminoterminal propeptide of type III procollagen (P-III-NP), monocyte chemoattractant protein-1, fibrin D-dimer, Growth-differentiation factor-15, Ischemia-modified albumin, lipoprotein-associated phospholipase A2, matrix metalloproteinases and CKMB. Of these additional biomarkers C-reactive protein, brain natriuretic protein and homocysteine are of particular interest.

In a specific embodiment of this aspect of the invention the additional biomarker is selected from the group consisting of C-reactive protein, ESR, carcinoembryonic antigen (CEA), CA-125, human epidermal growth factor receptor 2 (HER2), CA19-9, lactate dehydrogenase (LDH), tissue inhibitor metallo proteinase 1 (TIMP-1), brain natriuretic protein, interleukins, tumor necrosis factor-alfa, homocystein, amyloid A protein, Pregnancy-Associated Plasma Protein-A, troponines, soluble intercellular adhesion molecule-1, soluble UPAR, the aminoterminal propeptide of type III procollagen (P-III-NP), monocyte chemoattractant protein-1, fibrin D-dimer, Growth-differentiation factor-15, Ischemia-modified albumin, lipoprotein-associated phospholipase A2, matrix metalloproteinases and CKMB; more preferably selected from C-reactive protein, brain natriuretic protein and/or homocysteine.

The above mentioned embodiments may be comprised in a kit of parts together with any required medical and or sampling equipment and instructions for use of the equipment and how to perform the assay of choice.

Biological Sample

A biological sample is a sample obtained from a subject. As such a biological sample may be a sample selected from the group consisting of tissue, blood, serum, plasma samples, urine, cerebrospinal fluid, synovial fluid, ascites, and saliva. Of special relevance to the present invention are samples of blood, serum or plasma, more preferably the biological sample is serum or plasma. Those of ordinary skill in the art will be able to readily determine which assay sample source is the most appropriate for use in the diagnosis of a particular disease, or disorder or general state of health.

Subjects

The subjects herein referred to are single members of a species, herein preferably a mammalian species. Any mammalian species is an object of the present invention, although any of the following species are of particular relevance: mouse, rat, guinea pig, hamster, rabbit, cat, dog, pig, cow, horse, sheep, monkey, and human. Most preferably the subject of the present invention is a human. The subjects may in the present text also be referred to as patients or individuals.

Device

A further aspect of the present invention relates to a device for the diagnosis of the presence of a non-specific disease or disorder, wherein the device comprises means for measuring the level of YKL-40 in a sample; and means for comparing the measured level of YKL-40 with at least one reference level of YKL-40. The means for measuring the level of YKL-40 in a sample may for example be a test system that applies any of the above mentioned assay systems, such as an immunoassay, a PCR based assay or an enzymatic assay. An immunoassay is preferred for the present device.

A device according to the present invention may for example comprise a rapid, qualitative and/or quantitative test system mounted on a solid support for the determination of YKL-40 levels in biological samples.

The solid support can be used in any phase in performing any of the above assays, particularly immunoassays, including dipsticks, membranes, absorptive pads, beads, microtiter wells, test tubes, and the like. Preferred are test devices which may be conveniently used by the testing personnel or the patient for self-testing, having minimal or no previous training. Such preferred test devices include dipsticks and membrane assay systems. The preparation and use of such conventional test systems is well described in the patent, medical, and scientific literature. If a stick is used, the anti-YKL-40 antibody is bound to one end of the stick such that the end with the antibody can be dipped into or onto the biological samples. Alternatively, the samples can be applied onto the antibody-coated dipstick or membrane by pipette, dropper, tweezers or the like, or be squirted directly from the body and onto the stick. Accordingly, in a preferred embodiment of this aspect of the invention, the device is a dipstick.

In the present aspect of the invention any biological sample that is or may be converted to a fluid is preferred. Particularly biological samples that are obtainable from a body as a fluid are preferred; examples hereof include, and are not limited to: blood, serum, plasma, urine, cerebrospinal fluid, synovial fluid, ascites, semen, and saliva. More preferably serum and plasma samples.

The antibody against YKL-40 can be of any isotype, such as IgA, IgG or IgM, Fab fragments, or the like. The antibody may be a monoclonal or polyclonal and produced by methods as generally described in Harlow and Lane, Antibodies, A Laboratory Manual, Cold Spring Harbor Laboratory, 1988, incorporated herein by reference. See also section on immunoassays. The antibody can be applied to the solid support by direct or indirect means. Indirect bonding allows maximum exposure of the YKL-40 binding sites to the assay solutions since the sites are not themselves used for binding to the support. Polyclonal antibodies may be used since polyclonal antibodies can recognize different epitopes of YKL-40 thereby enhancing the sensitivity of the assay. Alternatively, monoclonal antibodies against YKL-40 may be used.

The solid support is preferably non-specifically blocked after binding the YKL-40 antibodies to the solid support. Non-specific blocking of surrounding areas can be with whole or derivatized bovine serum albumin, or albumin from other animals, whole animal serum, casein, non-fat milk, and the like.

The sample is applied onto the solid support with bound YKL-40-specific antibody such that the YKL-40 will be bound to the solid support through said antibodies. Excess and unbound components of the sample are removed and the solid support is preferably washed so the antibody-antigen complexes are retained on the solid support. The solid support may be washed with a washing solution which may contain a detergent such as Tween-20, Tween-80 or sodium dodecyl sulphate.

After the YKL-40 has been allowed to bind to the solid support, a second antibody which reacts with YKL-40 is applied. The second antibody may be labelled, preferably with a visible label. The labels may be soluble or particulate and may include dyed immunoglobulin binding substances, simple dyes or dye polymers, dyed latex beads, dye-containing liposomes, dyed cells or organisms, or metallic, organic, inorganic, or dye solids. The labels may be bound to the YKL-40 antibodies by a variety of means that are well known in the art. In some embodiments of the present invention, the labels may be enzymes that can be coupled to a signal producing system. Examples of visible labels include alkaline phosphatase, beta-galactosidase, horseradish peroxidase, and biotin. Many enzyme-chromogen or enzyme-substrate-chromogen combinations are known and used for enzyme-linked assays.

Simultaneously with the sample, corresponding steps may be carried out with a known amount or amounts of YKL-40 and such a step can be the standard for the assay.

The solid support is washed again to remove unbound labelled antibody and the labeled antibody is visualized and quantitated. The accumulation of label will generally be assessed visually. This visual detection may allow for detection of different colors, e.g., red color, yellow color, brown color, or green color, depending on label used. Accumulated label may also be detected by optical detection devices such as reflectance analyzers, video image analyzers and the like. The visible intensity of accumulated label could correlate with the concentration of YKL-40 in the sample. The correlation between the visible intensity of accumulated label and the amount of YKL-40 may be made by comparison of the visible intensity to a set of reference standards. Preferably, the standards have been assayed in the same way as the unknown sample, and more preferably alongside the sample, either on the same or on a different solid support. The concentration of standards to be used can range from about 1 µg of YKL-40 per liter of solution, up to about 1 mg of YKL-40 per liter of solution, preferably the range for testing serum samples will be from 40 µg/l to 400 µg/l YKL-40. Preferably, several different concentrations of YKL-40 standards are used so that quantitating the unknown by comparison of intensity of color is more accurate. An intensity of color similar to 110 µg/1 of YKL-40 may for example be considered negative, as compared with an intensity of color similar to 200 µg/l.

The device, such as the herein described dipstick or other solid support based test system, may thus be used in aid of determining the approximate level of YKL-40 in a biological sample by comparison to one or more standards/control fields. Thus the concentration of YKL-40 can be ascertained to be within a range between two of the concentrations of YKL-40 applied to the standard/control fields of the device. Alternatively the concentration of YKL-40 can be judged to be above or below a cut-off value of YKL-40, the chosen concentration for the cut-off value being applied to the control field of the dipstick. There may be multiple reference levels/standards available within and/or on the device or single reference level/standard within and/or on the device. In the latter case, the device may be used as a yes no test, to compare a YKL-level in a sample with one reference level, i.e. to see whether the YKL-level of the sample is above or below the reference level. In a preferred embodiment of a device according to the invention, the device comprises a single reference level, representing a cut-off value. The reference level may as any of the reference levels described herein above in the section termed "reference levels".

Although each of the steps can be carried out in the same vessel, such as a test tube, if it is cleaned and washed after each of the steps, a fast and convenient on-site assay is best performed according to the invention by using three separate vessels for each of the steps, one for the sample, one for washing, and one for developing the detectable label.

Figure 9:
FIGS. 9A and 9B Dipstick embodiments seen from above.
Figure 9:
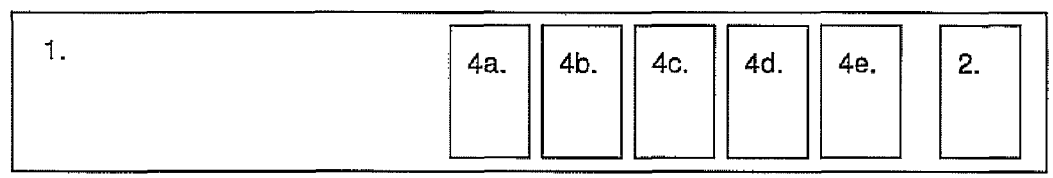

It is thus an object of the present invention that the YKL-40 level of a biological sample for use in the classification according to a reference level of YKL-40 of the individual from which the biological sample originated is measured by use of a dipstick. (see FIGS. 9A and 9B)

In an alternative embodiment of this aspect of the invention the device further comprises means for assaying additional biomarkers than YKL-40, such as any one or more of the biomarkers from the following non-limiting group: C-reactive protein (CRP), carcinoembryonic antigen (CEA), CA-125, human epidermal growth factor receptor 2 (HER2), CA19-9, lactate dehydrogenase (LDH), brain natriuretic protein (BNP), interleukins, tumor necrosis factor-alfa, homocysteine, amyloid A protein, Pregnancy-Associated Plasma Protein-A, troponines, soluble intercellular adhesion molecule-1, soluble UPAR, the aminoterminal propeptide of type III procollagen (P-III-NP), monocyte chemoattractant protein-1, fibrin D-dimer, Growth-differentiation factor-15, Ischemia-modified albumin, lipoprotein-associated phospholipase A2, matrix metalloproteinases, pentraxin 3, secretory phospholipase A2 group IIA, intercellular adhesion molecule-1, Heart-type fatty acid-binding protein (H-FABP), Myosin light chain-1 (MLC-1), P-selectin and CKMB. Preferably the device comprises means for assaying C-reactive protein and/or brain natriuretic protein and/or homocysteine.

In a specific embodiment of this aspect of the invention the device comprises means for assaying additional biomarkers selected from the group consisting of C-reactive protein, ESR, carcinoembryonic antigen (CEA), CA-125, human epidermal growth factor receptor 2 (HER2), CA19-9, lactate dehydrogenase (LDH), tissue inhibitor metallo proteinase 1 (TIMP-1), brain natriuretic protein, interleukins, tumor necrosis factor-alfa, homocystein, amyloid A protein, Pregnancy-Associated Plasma Protein-A, troponines, soluble intercellular adhesion molecule-1, soluble UPAR, the aminoterminal propeptide of type III procollagen (P-III-NP), monocyte chemoattractant protein-1, fibrin D-dimer, Growth-differentiation factor-15, Ischemia-modified albumin, lipoprotein-associated phospholipase A2, matrix metalloproteinases and CKMB; more preferably means for assaying C-reactive protein, brain natriuretic protein and/or homocysteine.

The at least one reference level in relation to the device may be any reference level of YKL-40 as described herein in the section "reference levels". In one specific embodiment of the device according to the invention, the device comprises a single reference level, representing a cut-off value.

In another specific embodiment of this aspect of the invention, the device comprises means for comparing the measured level of YKL-40 with at a set of age adjusted reference levels of YKL-40.

In another specific embodiment of this aspect of the invention, the device comprises means for comparing the measured level of YKL-40 with a set of age dependent cut-off values as defined in the following table:

| | Age dependent cut-off values for healthy subjects | | | | |
|---|---|---|---|---|---|
| Age intervals (years) | $70^{th}$ percentile (µg/l YKL-40) | $75^{th}$ percentile (µg/l YKL-40) | $85^{th}$ percentile (µg/l YKL-40) | $90^{th}$ percentile (µg/l YKL-40) | $95^{th}$ percentile (µg/l YKL-40) |
| 20-29 | 40 | 44 | 54 | 59 | 65 |
| 30-39 | 48 | 54 | 65 | 72 | 80 |
| 40-49 | 59 | 65 | 80 | 88 | 98 |
| 50-59 | 72 | 80 | 98 | 108 | 119 |
| 60-69 | 88 | 98 | 119 | 132 | 145 |
| 70-79 | 108 | 119 | 154 | 161 | 178 |
| 80-89 | 132 | 145 | 178 | 196 | 217 |

Kit of Parts

All the materials and reagents required for assaying YKL-40 according to the present invention can be assembled together in a kit, such kit includes at least elements in aid of assessing the level of YKL-40 in a biological sample obtained from an individual, and the instruction on how to do so.

Said elements may be a method of detecting the YKL-40 levels such as an immunoassay, or parts required to perform an immunoassay specific for YKL-40 detection. Optionally, a kit may further or alternatively comprise elements for performing PCR based assays for the detection of YKL-40 and determination of levels of the same from biological samples. The kit of parts may further comprise equipment for obtaining one or more biological samples, such equipment may for example be syringes, vials or other. The kit of parts may be packed for single use or for repeated usage, and the elements therein may be disposable such as to be disposed of after a single use or may be of a quality that allows repeated usage.

A further aspect of the present invention relates to a kit of parts comprising
  i) means for measuring the level of YKL-40 in a sample;
  ii) means for comparing the measured level of YKL-40 with at least one reference level of YKL-40; and
  iii) optionally instructions on how to age adjust the reference level of YKL-40, according to the age of the subject providing the sample.

The at least one reference level may be any reference level of YKL-40 as described herein in the section "reference levels".

Means for measuring the level of YKL-40 in a sample may include one or more solutions containing a known concentration of YKL-40, a washing solution, a solution of a chromogen which changes color or shade by the action of the enzyme directly or indirectly through action on a substrate, an anti-YKL-40 antibody conjugated to a label such that it could be detected, pipettes for the transfer of said solutions, test tubes for said solutions, and a solid support, in particular adapted to be inserted into the test tubes, carrying on the surface thereof a polyclonal antibody to YKL-40. The kit may also contain one or more solid support having an anti-YKL-40 antibody for use in assaying one or more samples simultaneously or individually, and the necessary reagent required to develop the label. Included in means for comparing the measured level of YKL-40 with at least one reference level of YKL-40 may be YKL-40 standards that can be assayed fresh along with the unknown sample. Such kits will comprise distinct containers for each individual reagent.

In the above test kit, the reagents may be supplied from storage bottles or one or more of the test tubes may be prefilled with the reagents or controls.

The components of the kit may also be provided in dried or lyophilized forms. When reagents or components are provided as a dried form, reconstitution generally is by the addition of a suitable solvent. It is envisioned that the solvent also may be provided in another container means.

The kits of the present invention also will typically include a means for containing the reagents such as vials or tubes in close confinement for commercial sale such as, e.g. injection or blow-molded plastic containers into which the desired vials are retained. The kits will also comprise a set of instructions on how to perform the assay.

In an alternative embodiment of this aspect of the invention the kit will comprise means for assaying additional biomarkers than YKL-40, such as any one or more of the biomarkers from the following non-limiting group: C-reactive protein (CRP), carcinoembryonic antigen (CEA), CA-125, human epidermal growth factor receptor 2 (HER2), CA19-9, lactate dehydrogenase (LDH), brain natriuretic protein (BNP), interleukins, tumor necrosis factor-alfa, homocysteine, amyloid A protein, Pregnancy-Associated Plasma Protein-A, troponines, soluble intercellular adhesion molecule-1, soluble UPAR, the aminoterminal propeptide of type III procollagen (P-III-NP), monocyte chemoattractant protein-1, fibrin D-dimer, Growth-differentiation factor-15, Ischemia-modified albumin, lipoprotein-associated phospholipase A2, matrix metalloproteinases, pentraxin 3, secretory phospholipase A2 group IIA, intercellular adhesion molecule-1, Heart-type fatty acid-binding protein (H-FABP), Myosin light chain-1 (MLC-1), P-selectin and CKMB.

In a specific embodiment of this aspect of the invention the kit comprises means for assaying additional biomarkers selected from the group consisting of C-reactive protein, ESR, carcinoembryonic antigen (CEA), CA-125, human epidermal growth factor receptor 2 (HER2), CA19-9, lactate dehydrogenase (LDH), tissue inhibitor metallo proteinase 1 (TIMP-1), brain natriuretic protein, interleukins, tumor necrosis factor-alfa, homocystein, amyloid A protein, Pregnancy-Associated Plasma Protein-A, troponines, soluble intercellular adhesion molecule-1, soluble UPAR, the aminoterminal propeptide of type III procollagen (P-III-NP), monocyte chemoattractant protein-1, fibrin D-dimer, Growth-differentiation factor-15, Ischemia-modified albumin, lipoprotein-associated phospholipase A2, matrix metalloproteinases and CKMB; more preferably means for assaying C-reactive protein, brain natriuretic protein and/or homocysteine.

Preferably the kit will comprise means for assaying C-reactive protein and/or brain natriuretic protein and/or homocysteine.

The kit according to the present invention may furthermore comprise a device according to the invention as described above here in the section termed "device".

All patent and non-patent references cited in the present application, are hereby incorporated by reference in their entirety.

EXAMPLES

The following examples are for illustrative purposes only and should not be construed as limiting the scope of the invention, which is defined by the appended claims.

Example 1

Plasma YKL-40 Levels in Normal Subjects and Plasma YKL-40 as an Independent Risk Factor Methods
Participants We used a population-based prospective study of the Danish general population, the 1991-1994 examination of the Copenhagen City Heart Study (Bojesen et al, 2003; Nordestgaard et al, 2007; Schnohr et al, 2002). Participants aged 20 years and above were selected randomly after gender and age stratification into 5-year groups among residents of Copenhagen. Of the 17180 subjects invited, 10135 participated, and plasma was available for YKL-40 determination in 8899 participants. Participants were followed for 16 years using their unique Central Person Registry number from baseline at the 1991-1994 examination until July 2007. Follow-up was 100% complete. Roughly 99% were Caucasians of Danish descent. At time of blood sampling (1991-1994), 1763 participants had a disease known to be associated with increased levels of plasma YKL-40 (cancer, ischaemic cardiovascular disease, liver disease, diabetes, chronic obstructive pulmonary disease, asthma, rheumatoid arthritis, inflammatory bowel disease or pneumonia). During follow-up additional 3526 had developed at least one of these diseases. 3059 had died. Leaving 3610 healthy participants at the end of follow-up.

Plasma YKL-40 was measured a second time in blood samples of 929 participants of the 2001-2003 examination of the Copenhagen City Heart Study cohort. These participants were selected as having no known disease at the 1991-1994 and 2001-2003 examination, allowing correction for regression dilution bias (Clarke R, 1999).

The participants filled out a self-administered questionnaire, which was validated by the participant and an investigator on the day of attendance. Participants reported on smoking habits and subdivided into never, previous and current smoker.

Endpoints

Information on death and morbidity were collected from three different population registries using the participants' unique national Danish Central Person Registry number. Information on death was obtained from the national Danish Civil Registry System (Juel et al, 1999). Information on morbidity in ICD8 and ICD10 codes from 1976 until July 2007 was obtained from the national Danish Patient Registry (34) and subdivided into the following diagnoses associated with increased levels of plasma YKL-40: ischaemic cardiovascular disease, liver disease, diabetes, chronic obstructive pulmonary disease, asthma, rheumatoid arthritis, inflammatory bowel disease or pneumonia. Diagnoses of cancer were obtained from the national Danish Cancer Registry (from 1947 until 2004), which identifies 98% of all cancers in Denmark (35,36) and the national Danish Patient Registry (from 2004 until July 2007).

Ethics

All participants gave written informed consent. The study was approved by Herlev Hospital and a Danish ethical committee (No. 100.2039/91 and 01-144/01, Copenhagen and Frederiksberg committee) and conducted according to the Declaration of Helsinki.

YKL-40 Analysis

Plasma levels of YKL-40 were determined in duplicates in samples frozen for 12-15 years at −80° C. by a commercial two-site, sandwich-type enzyme-linked immunosorbent assay (ELISA) (Quidel Corporation, San Diego, Calif.) (Harvey et al, 1998), using streptavidin-coated microplate wells, a biotinylated-Fab monoclonal capture antibody, and an alkaline phosphatase-labeled polyclonal detection antibody. The recovery of the ELISA was 102% and the detection limit 10 µg/L. The intra-assay coefficients of variations were 5% (at 40 µg/L), 4% (at 104 µg/L), and 4% (at 155 µg/L). The inter-assay coefficient of variation was <6%.

Statistical Analysis

We used STATA version 10.0 (Stata Corp LP, College Station, Tex.). Two-sided P<0.05 was considered significant. Mann-Whitney rank-sum test and Spearman's rho correlation were used. Plasma YKL-40 levels were stratified into categories according to plasma YKL-40 percentiles in gender and 10-year age-groups: the percentile categories were 0-33%, 34-66%, 67-90%, 91-95%, and 96-100%. In Table 3 only three percentile categories were used 0-33%, 34-90%, and 91-100%.

Kaplan-Meier curves plotted cumulative survival against left-truncated age and follow-up time in all participants. Kaplan-Meier curves also plotted cumulative survival in subgroups of participants with cancer, ischaemic cardiovascular disease, liver disease, diabetes, chronic obstructive pulmonary disease, and asthma against follow-up time. Differences between plasma YKL-40 percentile categories were examined using log-rank tests. Hazard ratios and 95% confidence intervals for death were calculated using Cox regression analysis. Hazard ratios were adjusted for other risk factors such as gender, age (deciles) and smoking habits (never/previous/current smokers) at the time of blood sampling. For trend-test, increasing plasma YKL-40 categories labelled 0, 1, 2, 3, and 4 or 0, 1, and 2 (only for the results in Table 3) were used as a continuous variable in the Cox regression. P-values for the trend-test were calculated using the Chi-square value (1 df) of the likelihood-ratio test of the model without YKL-40 categories nested in the model with YKL-40 categories. We tested for proportionality of hazards over time based on Schonefeld residuals and found no violation. Information on baseline covariates was more than 99% complete; individuals with incomplete information on covariates were excluded from multifactorial analysis. Hazard ratios were corrected for regression dilution bias using a non-parametric method (Clarke et al, 1999). For this correction we used plasma YKL-40 values from 929 healthy individuals attending both the 1991-1994 baseline examination and the 2001-2003 follow-up examination; however, the main analysis were conducted on all 8899 participants. A regression dilution ratio of 0.8042 was computed.

Absolute 10-year mortality by plasma YKL-40 percentile categories was estimated by using the regression coefficients from a Poisson regression model including the following covariates: Gender, age (<50, 50-70, >70 years), and smoking habits (never, previous, current smokers) at time of blood sampling. Absolute mortality is presented as estimated incidence rates (events/10 years) in percentages.

Results

Plasma YKL-40 in Healthy Participants

The study population consisted of 8899 participants (56% women), aged from 20 to 95 years with a mean of 59 years. Baseline characteristics of all participants according to plasma YKL-40 percentile categories adjusted for age and sex are given in Table 4. 7136 (80%) participants had no known disease at the time of blood sampling in 1991-1994. During the 16 years follow-up period 3576 developed disease leaving 3610 healthy participants at the end of follow-up. The median plasma YKL-40 in these healthy participants was 42 µg/L (2.5%-97.5% percentile range: 14-168 µg/L; 90% percentile 92 µg/L; 95% percentile 124 µg/L). Plasma YKL-40 levels increased in both sexes with increasing age (trend test p<0.0001) (FIG. 1). Spearman's rho correlation between plasma YKL-40 and age was 0.41 (p<0.0001). There was no difference between plasma YKL-40 in women and men (Mann-Whitney U; p=0.27).

Figure 2:
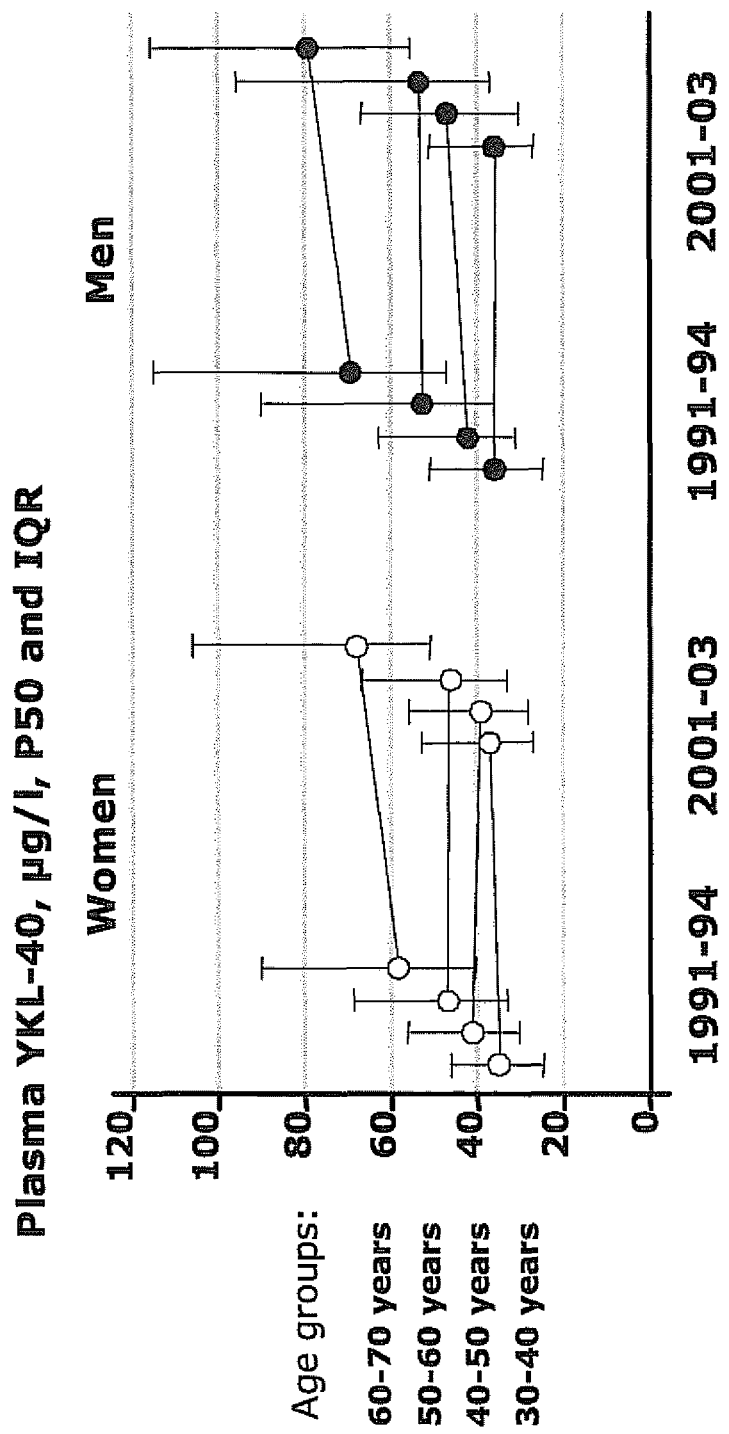
FIG. 2. Plasma concentrations of YKL-40 in a group of 929 healthy participants (463 women and 466 men), who had their first YKL-40 measurement in the blood from the 1991-1994 examination and the second YKL-40 measurement in the blood from the 2001-2003 examination. The mean increase was 0.5 μg/L/year (interquartile range −0.6-2.1 μg/L/year) in women and 0.8 μg/L/year (−0.3-2.9 μg/L/year) in men. This illustrates that plasma YKL-40 is very stable in subjects that remain healthy and a regression dilution ratio of 0.8042 was computed. There was no statistically difference between men and women.

Plasma concentrations of YKL-40 in a group of 929 healthy participants (463 women and 466 men), who had their first YKL-40 measurement in the blood from the 1991-1994 examination and the second YKL-40 measurement in the blood from the 2001-2003 examination can be seen from FIG. 2. The mean increase was 0.5 µg/L/year (interquartile range −0.6-2.1 µg/L/year) in women and 0.8 µg/L/year (−0.3-2.9 µg/L/year) in men. This illustrates that plasma YKL-40 is very stable in subjects that remain healthy and a regression dilution ratio of 0.8042 was computed. There was no statistically difference between men and women.

Plasma concentrations of YKL-40 in a group of 2116 healthy women and 1494 healthy men, which had no known disease at the time of blood sampling in 1991-1994 and remained healthy during the 16 years follow-up period (i.e. none were dead or had develop cancer, ischaemic cardiovascular disease, liver disease, diabetes, chronic obstructive pulmonary disease, asthma, rheumatoid arthritis, inflammatory bowel disease, and pneumonia) can be seen from FIG. 3. The figure illustrates the mean plasma YKL-40 in these healthy participants, the 70% percentile (defined as ln(plasma YKL-40)=3.1+0.02×age (years)), the 75% percentile (defined as ln(plasma YKL-40)=3.2+0.02×age (years)), the 90 percentile (defined as ln(plasma YKL-40)=3.5+0.02×age (years)) and the 95% percentile (defined as ln(plasma YKL-40)=3.6+0.02×age (years)) according to age. Women and men were combined.

In contrast to serum CRP (Kushner et al, 2006) we found no difference in plasma YKL-40 between sexes. Furthermore, we demonstrated in a large group of healthy participants that plasma YKL-40 remained stable over time.

The median increase of plasma YKL-40 in the group of 929 healthy participants (463 women and 466 men), who had their first YKL-40 measurement in the blood from the 1991-1994 examination and the second YKL-40 measurement in the blood from the 2001-2003 examination was 0.5 μg/L/year (interquartile range −0.6-2.1 μg/L/year) in women and 0.8 μg/L/year (−0.3-2.9 μg/L/year) in men. The difference between men and women was not significant.

The median plasma concentrations of YKL-40 are higher for the participants with incident events (cancer, ischaemic cardiovascular disease, liver disease, diabetes, chronic obstructive pulmonary disease, and asthma) than for the participants who stay healthy (Table 1).

Since minor elevations in serum C-reactive protein (CRP), a inflammatory biomarker, have been shown to predict death in both healthy and diseased individuals (Kushner et al, 2006) we also examined the predictive value of plasma YKL-40 in the participants with low plasma CRP (i.e. ≤1.75 mg/L). It was examined whether the predictive value of plasma YKL-40 concentration was independent of CRP. In the 4453 participants with low plasma CRP concentrations (i.e. ≤1.75 mg/L) the hazard ratios for death were 1.0 (95% CI, 0.8-1.2) for plasma YKL-40 percentile category 34-66%, 1.4 (1.1-1.7) for plasma YKL-40 category 67-90%, 2.3 (1.6-3.3) for category 91-95%, and 3.4 (2.5-4.8) for category 96-100% versus plasma YKL-40 percentile category 0-33% ($\log_{10}$ p for trend 12.1). Similar results were found in the participants with plasma CRP>1.75 mg/L ($\log_{10}$ p for trend 18.3) (Table 2). Accordingly, in these subjects the hazard ratios for death increased highly significant with increasing plasma YKL-40 levels, confirming that plasma YKL-40 is independent of plasma CRP.

Elevated plasma YKL-40 and increased risk of death was not related to a specific type of disease, but was found in participants diagnosed with cancer, ischaemic cardiovascular disease, liver disease, diabetes, and chronic obstructive pulmonary disease either before the time of blood sampling in 1991-1994 or during the 16 years follow-up period.

The association between increasing plasma YKL-40 and increased risk of death was similar, or higher, than that of smoking status and risk of death. Furthermore, multivariate cox analysis including smoking status, age and sex demonstrated that plasma YKL-40 was an independent risk factor, i.e. it was shown that plasma YKL-40 percentile category was a risk factor for early death independent of age, gender, plasma CRP, smoking status or disease (cancer, ischemic cardiovascular disease, and other diseases associated with elevated plasma YKL-40). Increasing plasma YKL-40 was associated with smoking (trend, p=0.0005).

In this study of adults from the Danish general population we found that elevated plasma concentrations of YKL-40 predicted early death. The difference in the median survival age between participants with elevated plasma YKL-40 compared to low plasma YKL-40 was 14 years, and the difference in the percentage of participants alive at 15-years follow-up after the time of blood sampling between these two groups was 26%.

It is a strength of the study that the predictive value of plasma YKL-40 was evaluated in a large cohort of well characterized subjects, with a long follow-up period, and with no losses to follow-up.

Plasma YKL-40 as a Risk Factor of Death in the General Population

Figure 4A:
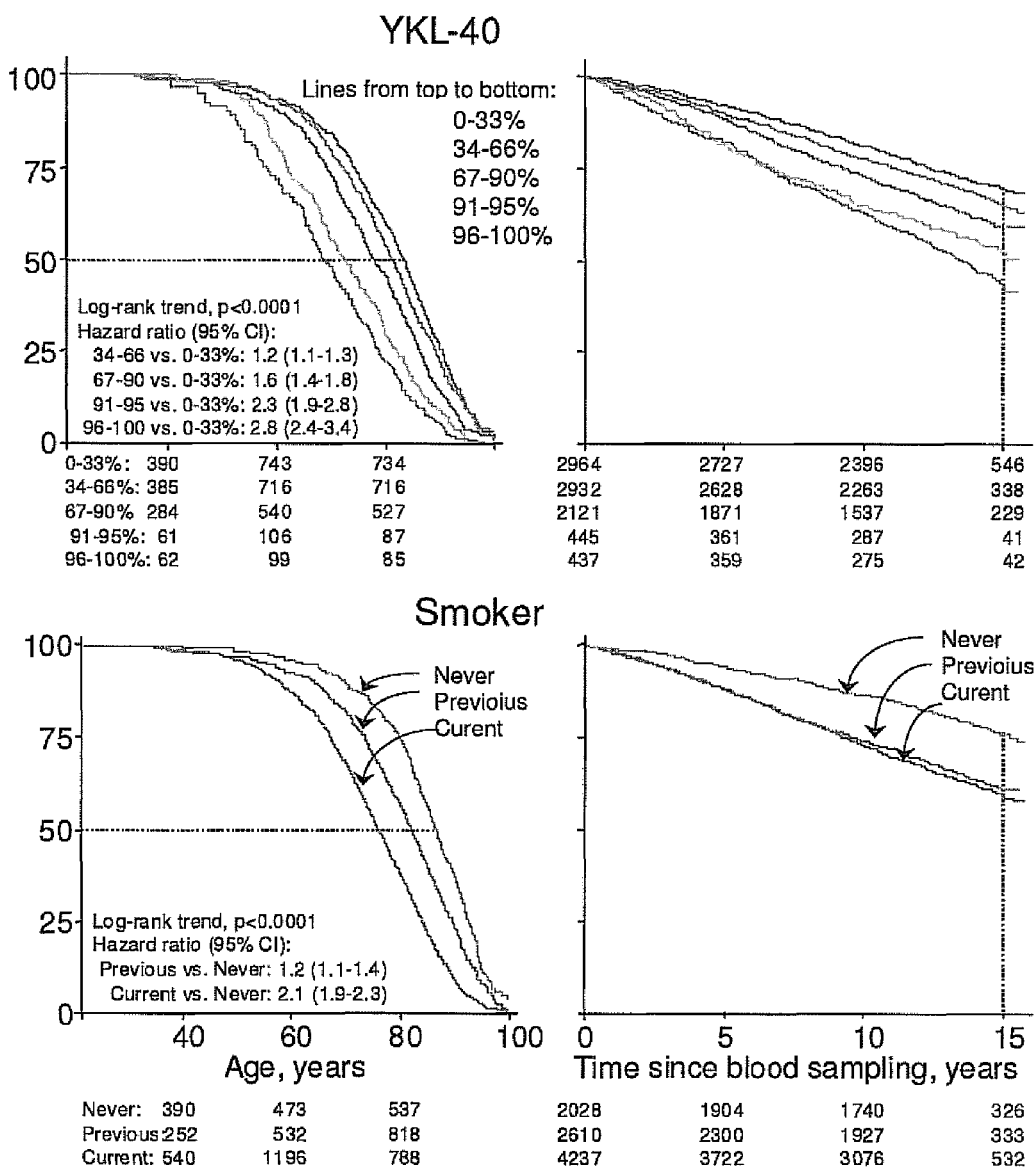
FIG. 4A. Longevity and survival of the general population according to increasing plasma concentrations of YKL-40 (divided into five gender and 10-year age percentile categories: 0-33% percentile, 34-66%, 67-90%, 91-95%, and 96-100%). Left-truncated age and follow-up time were the underlying time-scales, respectively. Follow-up started at time of blood sampling and ended at death or July 2007, whichever came first. Women and men are combined. For comparison the effect of smoking status in the same population is shown.

During 16 years follow-up, 3059 of the 8899 participants died. Increasing plasma YKL-40 (divided into five gender and 10-year age percentile categories) was associated with increasing risk of early death of all causes (log rank test, $p=3.8*10^{-46}$) (Table 3 and FIG. 4A). Participants with low plasma YKL-40 (percentile 0-33%) vs. participants with high plasma YKL-40 (percentile 96-100%) had a longer median survival age of 83 years vs. 69 years and a higher 15-year survival of 70% vs. 44%. Thus, the effect on median survival age and 15-year survival of increasing plasma YKL-40 was similar or even higher than that of smoking status (Table 3 and FIG. 4A).

Multifactorially adjusted (sex, age, and smoking status at time of blood sampling) hazard ratios for overall death were 1.2 (95% CI, 1.1-1.3) for plasma YKL-40 percentile category 34-66%, 1.6 (1.4-1.8) for 67-90%, 2.3 (1.9-2.8) for 91-95%, and 2.8 (2.4-3.4) for plasma YKL-40 percentile category 96-100% versus plasma YKL-40 percentile category 0-33% (p-trend, $p=1.0*10^{-37}$). These estimates remained constant after adjusting for violent death (Table 2). Hazard ratios (HR) for death were calculated according to plasma YKL-40 in gender and 10-year age percentile categories.

In participants with cancer, in participants with ischaemic cardiovascular death and in participants with other diseases, highly significant associations were also found between increasing plasma YKL-40 percentile categories and increasing multifactorially adjusted hazard ratios for risk of death ($\log_{10}$ p for trend 11.4, 12.5, and 15.1, respectively) (Table 2).

Absolute 10-Year Mortality

Figure 4B:
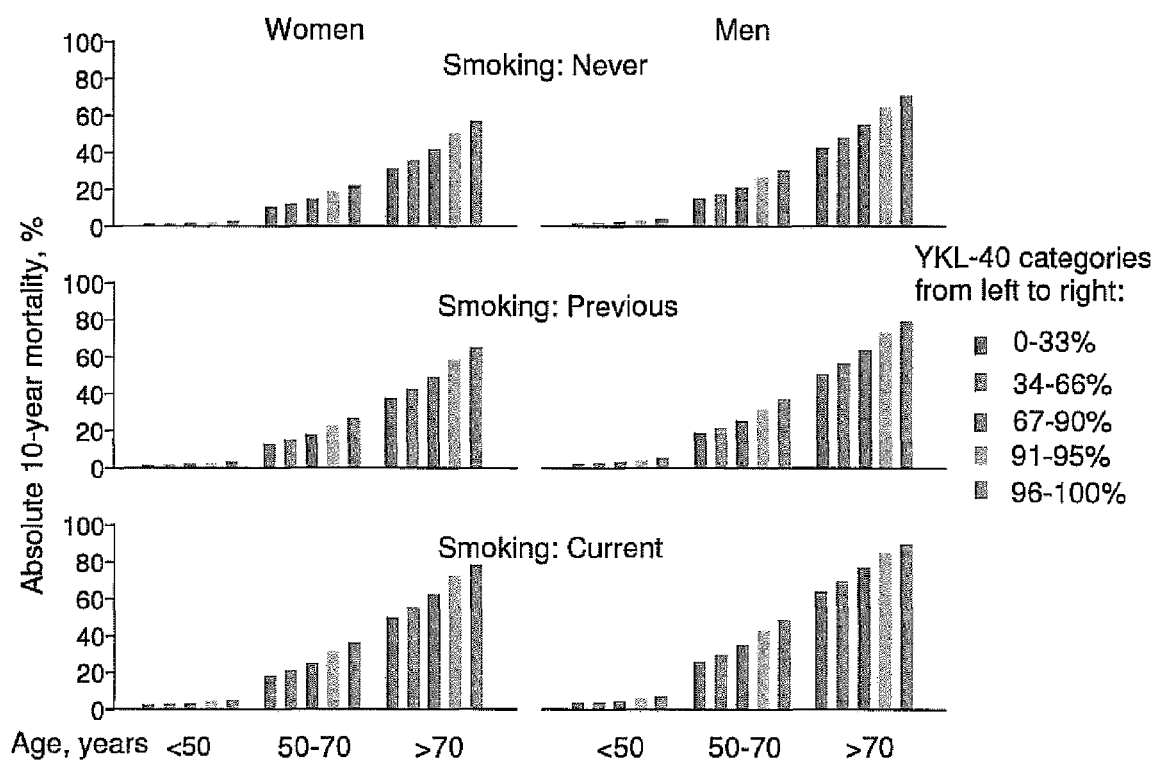
FIG. 4B. Absolute 10-year mortality according to plasma YKL-40 percentile categories, smoking status, gender and age. Based on 8899 participants from the Copenhagen City Hearth Study 1991-1994 examination followed for 16 years. P-values are test for log-rank trend. Plasma YKL-40 percentile categories 0-33%, 34-66%, 67-90%, 91-95%, and 96-100%, are given from left to right for each of the age groupings <50 years, 50-70 years, and >70 years.

The lowest absolute 10-year mortality was 1.2% in never smoking women aged <50 years in the plasma YKL-40 percentile category 0-33% (FIG. 4B). Absolute 10-year mortality was higher in men than in women and increased with increasing age and from never through previous to current smoking status. The highest absolute 10-year mortality was 78% and 90% in smoking women and men aged >70 years and in the 96-100% plasma YKL-40 percentile category (FIG. 4B).

In conclusion, in this large prospective study of subjects from the general population we found a strong association between elevated plasma concentrations of YKL-40 and early death, independent of smoking.

TABLE 1

Status of study participants from the general population and plasma YKL-40 concentration

| | | | Participants with event during follow-up | | | | | |
|---|---|---|---|---|---|---|---|---|
| | At blood | Median | Sex and 10-year age-groups percentiles of plasma YKL-40, n (%) | | | | | During follow- |
| Status | sampling, n | (IQR), µg/l | 0-33% | 34-66% | 67-90% | 91-95% | 96-100% | up, n |
| Healthy | 7136 | 42 (30-61) | 1364 (38) | 1247 (35) | 759 (21) | 138 (4) | 102 (3) | 3610 |
| Any disease* | 1763 | 67 (42-110) | 1121 (32) | 1117 (32) | 883 (25) | 207 (6) | 198 (6) | 3526 |
| Cancer | 704 | 65 (42-107) | 528 (34) | 509 (32) | 376 (24) | 83 (5) | 79 (5) | 1575 |
| Ischaemic cardiovasc. disease | 664 | 73 (46-116) | 455 (30) | 491 (33) | 397 (27) | 79 (6) | 76 (5) | 1498 |
| Liver disease | 81 | 96 (49-217) | 30 (20) | 37 (25) | 27 (18) | 20 (13) | 37 (25) | 151 |
| Diabetes | 156 | 71 (45-128) | 147 (28) | 159 (30) | 147 (28) | 36 (7) | 42 (8) | 531 |
| Chronic obstruct. pulm. disease | 155 | 71 (46-122) | 252 (29) | 251 (29) | 237 (28) | 51 (6) | 68 (8) | 859 |
| Asthma | 93 | 56 (39-96) | 98 (34) | 88 (31) | 67 (23) | 20 (7) | 15 (5) | 288 |

*Death (only incident), cancer, ischaemic cardiovascular disease, liver disease, diabetes, chronic obstructive pulmonary disease, asthma, rheumatoid arthritis, inflammatory bowel disease, pneumonia. Some participants had more than one disease.
IQR, interquartile range.

TABLE 2

Hazard ratios for death and plasma YKL-40 concentration

| | Participants/ | Hazard ratio* by sex and 10-year age-groups percentiles of YKL-40 | | | | | $-\log_{10}$ |
|---|---|---|---|---|---|---|---|
| Population/Event | Events | 0-33% | 34-66% | 67-90% | 91-95% | 96-100% | (p-trend) |
| All§/Death | 8875/3047 | 1.0 | 1.2 (1.1-1.3) | 1.6 (1.4-1.8) | 2.3 (1.9-2.8) | 2.8 (2.4-3.4) | 37.3 |
| All§/Non-violent death | 8804/2976 | 1.0 | 1.2 (1.1-1.3) | 1.6 (1.4-1.8) | 2.3 (1.9-2.8) | 2.8 (2.4-3.4) | 36.8 |
| All§/Violent death | 8875/71 | 1.0 | 1.6 (0.8-3.2) | 1.2 (0.5-2.8) | 1.9 (0.5-7.1) | 2.6 (0.8-8.8) | 0.7 |
| Never-smokers/Death | 2028/450 | 1.0 | 1.1 (0.8-1.4) | 1.6 (1.2-2.2) | 2.5 (1.5-4.2) | 3.6 (2.1-6.1) | 7.2 |
| Ever-smokers/Death | 6847/2597 | 1.0 | 1.2 (1.1-1.4) | 1.6 (1.4-1.8) | 2.2 (1.8-2.7) | 2.7 (2.2-3.3) | 30.4 |
| Plasma CRP-conc.¶ ≤1.75 mg/L/Death | 4453/1081 | 1.0 | 1.0 (0.8-1.2) | 1.4 (1.1-1.7) | 2.3 (1.6-3.3) | 3.4 (2.5-4.8) | 12.1 |
| Plasma CRP-conc.¶ >1.75 mg/L/Death | 4404/1958 | 1.0 | 1.3 (1.1-1.5) | 1.5 (1.3-1.8) | 2.1 (1.6-2.6) | 2.4 (1.9-3.0) | 18.3 |
| Participants with cancer§/Death | 2271/1400 | 1.0 | 1.1 (1.0-1.3) | 1.4 (1.2-1.6) | 2.1 (1.5-2.8) | 2.4 (1.8-3.1) | 11.4 |
| Participants with ischaemic cardiovascular disease§/Death | 2158/1327 | 1.0 | 1.2 (1.0-1.5) | 1.5 (1.2-1.8) | 2.4 (1.8-3.3) | 2.3 (1.7-3.1) | 12.5 |
| Participants with other diseases§**/Death | 2820/1599 | 1.0 | 1.2 (1.0-1.4) | 1.4 (1.2-1.7) | 2.0 (1.5-2.5) | 2.4 (1.9-3.0) | 15.1 |

§For 24 participants smoking status was unknown.
¶For additional 18 participants plasma concentration of CRP was unknown.
*Hazard ratios were adjusted for other risk factors such as gender, age (deciles) and smoking habits (never/previous/current smokers) at time of blood sampling, corrected for regression dilution bias.
CRP = C-reactive protein.
**Benign liver disease, diabetes, chronic obstructive pulmonary disease and asthma, rheumatoid arthritis, inflammatory bowel diasease, pneumonia. Some participants had more than one disease.

TABLE 3

Median survival age and 15-year survival in participants from the general population according to plasma YKL-40 percentile category or smoking status#.

| Risk factor | Median survival age, years (95% confidence interval) | 15-year survival, % (95% CI) |
|---|---|---|
| YKL-40 | | |
| 96-100% | 69 (66-72) | 44 (39-49) |
| 91-95% | 73 (69-75) | 52 (47-58) |
| 67-90% | 78 (77-80) | 59 (57-62) |
| 34-66% | 81 (80-82) | 66 (64-67) |
| 0-33% | 83 (82-84) | 70 (68-71) |
| Smoking | | |
| Current | 76 (75-77) | 60 (58-61) |
| Previous | 82 (81-83) | 61 (59-63) |
| Never | 87 (86-88) | 76 (74-78) |

Based on 8899 participants from The Copenhagen City Heart Study 1991-1994 examination followed for 16 years.

TABLE 4

Baseline characteristics of study participants from the general population¤

| Characteristics | Categories by sex and 10-year age plasma YKL-40 percentile | | | | | P Trend |
|---|---|---|---|---|---|---|
| | 0-33% | 34-66% | 67-90% | 91-95% | 96-100% | |
| Number (%) | 2964 (33) | 2932 (33) | 2121 (24) | 445 (5) | 437 (5) | — |
| Women, % | 57 | 56 | 56 | 56 | 57 | 0.96 |
| Age, years | 61 (48-71) | 61 (48-71) | 61 (48-71) | 60 (48-71) | 61 (48-71) | 0.12 |
| Current smokers, % | 43 | 48 | 51 | 56 | 58 | 0.0005 |

¤Values were collected at the 1991 through 1994 examination of the Copenhagen City Heart Study, and expressed as number, percent, or median (inter-quartile range). Statistical comparisons between the five YKL-40 percentile categories were made using trend test (YKL-40 categories were coded 0, 1, 2, 3, and 4 for increasing percentile categories).

Example 2

Diurnal, Weekly and Long Time Variation in Serum Concentrations of YKL-40 in Healthy Subjects Materials and Methods
Reference Interval Serum was collected from 245 healthy subjects (women/men 134/111, median age 49 years, range 18-79).

Diurnal Variation

Serum was collected seven times during a 24 hour period (day 1: 10 AM, 1 PM, 4 PM, 7 PM, 10 PM; day 2: 7 AM, 10 AM) from 16 healthy subjects (10/6, 48 years, range 32-66).

Day-to-Day Variation over 3 Weeks

Serum was collected at 8 AM five times during a 3 week period (day 1, 2, 8, 15, and 22) from 38 subjects recruited from the hospital staff (21/17, 41 years, range 22-66). At day 8 samples were also collected at 2 PM.

Week-to-Week Variation Over 2 Years

Serum was collected from 23 subjects recruited from the hospital staff (14/9, 42 years, range 31-66) at 8 AM five times during a 3 week period (day 1, 2, 8, 15, and 22) and repeated 6, 12 and 24 months later.

Variation Over 3 Years

Serum was collected between 8 AM and 10 AM five times during a 4 week period (day 1, 8, 15, 22 and 29) from 30 healthy women (48 years, range 24-62), and repeated 3 years later in 21 of the subjects.

Variation After Exercise

Serum was collected before physical exercise, immediately after a biphasic 25 minutes exercise program using an ergometer bicycle, and 1 and 3 hours post-exercise from 14 healthy subjects (10/4, 50 years, range 35-64). The healthy subjects included in the present study had no previous medical history, did not experience any symptoms and had no signs of disease and were not taking any medicine.

Ethics

The studies were approved by the regional scientific ethical committee and carried out in accordance with the Declaration of Helsinki. The subjects were informed about the studies verbally and in writing and all gave their written informed consent. All were informed that they could stop the study at any time.

YKL-40 ELISA

Proper handling of blood samples are important to minimize changes in serum YKL-40 that are not related to disease processes but represent metodological variability (Johansen et al., 2006, A; Johansen et al., 2006, B; and Harvey et al., 1998). Blood samples were allowed to clot at room temperature, centrifuged within ½-2 hours at minimum 2500 g for 10 minutes and serum was stored at −80° C. until analysis.

Serum YKL-40 was determined in duplicates by a commercial two-site, sandwich-type enzyme-linked immunoassay (ELISA) (Quidel Corporation, San Diego, Calif.) using streptavidin-coated microplate wells, a biotinylated-Fab monoclonal capture antibody, and an alkaline phosphatase-labeled polyclonal detection antibody (Harvey et al., 1998). The recovery of the ELISA was 102% and detection limit 20 µg/L (Johansen et al., 2006, B; and Harvey et al., 1998). The intra-assay coefficient of variation (CV) was ≤5.0% and inter-assay CVs≤10.2% (personal observation). Samples from each subject were analyzed on the same ELISA plate.

Statistical Analysis

Descriptive statistics for serum YKL-40 were presented by the median or the geometric mean, coefficient of variation and 95% confidence interval and range. The distribution of serum YKL-40 is skewed and therefore the log transform (natural) is used for statistical estimation. The reference interval was estimated using linear regression with YKL-40 on the log scale. The variations in serum YKL-40 analysed over time (variability during 24 hours, over 3 weeks, 6 months, 12 months, 24 months and 3 years) were given by the CV and compared to the intra- and inter-assay CV of the YKL-40 ELISA. The variance components for within subjects, between subjects and between rounds were estimated assuming a random effects model with YKL-40 log transformed (multiplicative model) and presented by the coefficient of variation of the geometric means (Kirkwood, 1979). The 95% confidence limits for the difference between 2 measurements of YKL-40 in an individual were calculated on the log scale and back transformed. The relative homogeneity between subjects compared to the total variation was estimated by the intraclass correlation coefficient. Serum YKL-40 in the analysis of diurnal long term variation and physical activity were analysed using a general linear model with repeated measures. P-values<5% were considered significant. P-values for multiple testing were corrected using the Boneferroni correction. All statistical calculations were done using SAS (9.1, SAS Institute, Cary, N.C., USA).

Results

In healthy subjects the median serum YKL-40 was 43 µg/l (range: 20-184 µg/L; 5-95% interval: 20-124), and no difference between men and women (P=0.54). Serum YKL-40 increased with age (rho=0.45; P<0.0001). A normal reference interval for serum YKL-40 adjusted for age and gender was constructed by linear regression with serum YKL-40 as the dependent variable (log transformed) and age and gender as the explanatory variables. The upper limit was defined as the 95th percentile for given age and gender. The inter subject CV adjusted for age was 45%.

Figure 5:
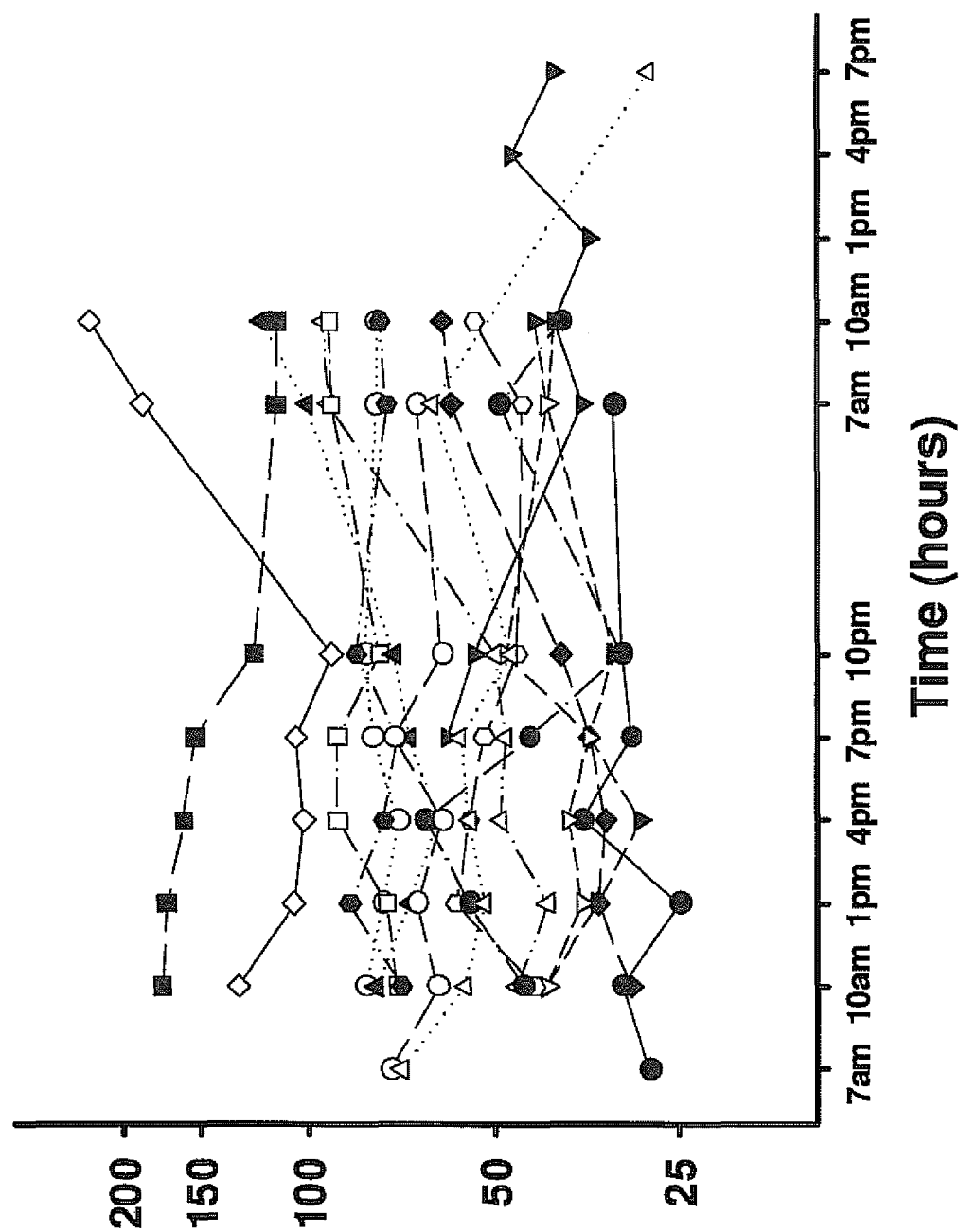
FIG. 5. Individual diurnal variation in serum concentrations of YKL-40 in 16 healthy subjects.

FIG. 5 illustrates the individual diurnal variation in serum YKL-40 at 7 time points during 24 hours. The mean serum YKL-40 increased 23% from 10 AM to 10 PM (P=0.01), however nonsignificant when corrected for multiple testing. No other significant differences were observed.

No changes in serum YKL-40 were found after 25 minutes of bicycling (P>0.08, linear model).

Figure 6:
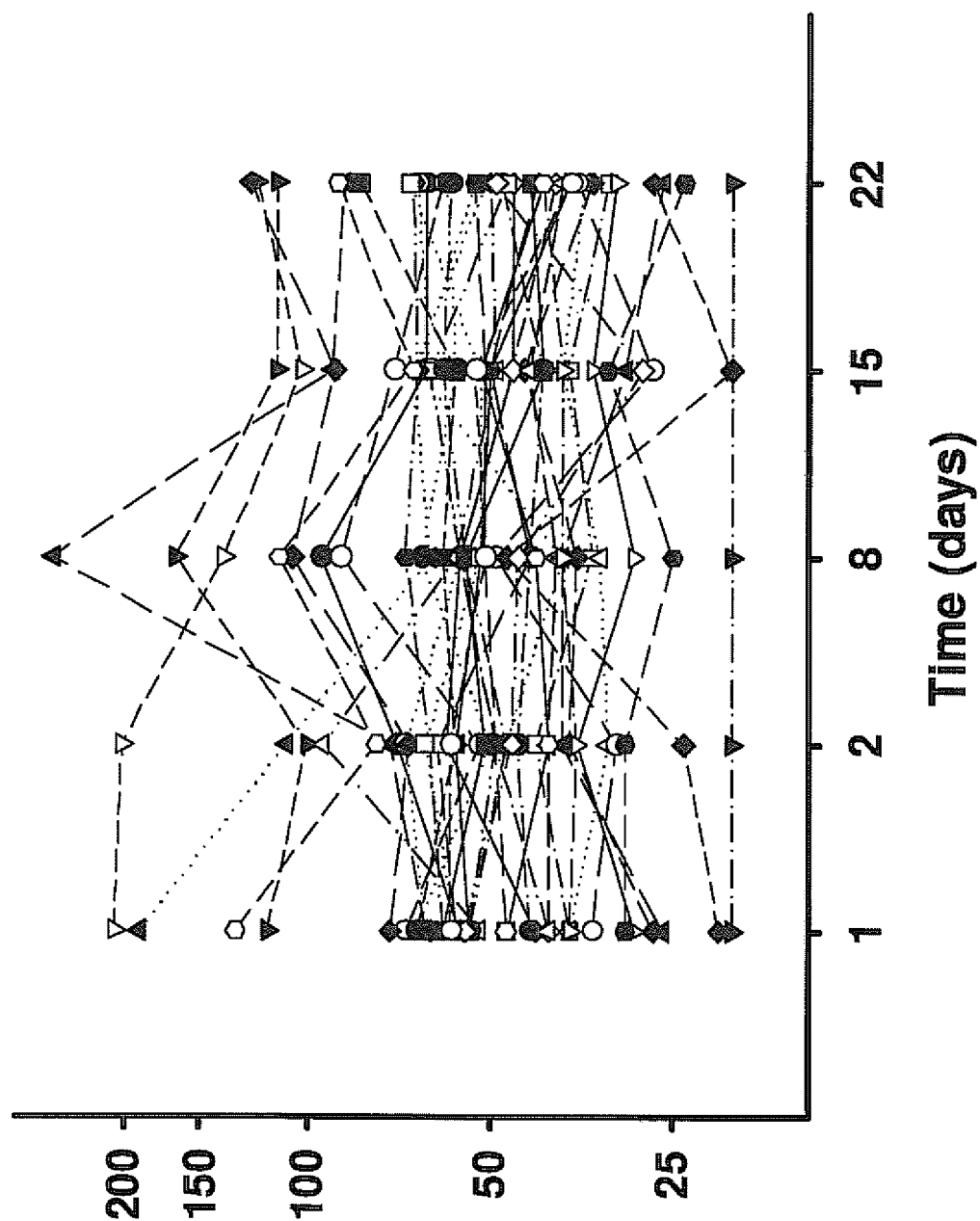
FIG. 6. Individual variation in serum YKL-40 levels of 38 healthy subjects over a period of 3 weeks.

FIG. 6 shows the individual weekly changes in serum YKL-40 at 6 time points during a 3 weeks period (at 8 AM on day 1, 2, 8, 15 and 22). The median day to day CV of serum YKL-40 for each subject was 16%. On day 8 samples were collected at 8 AM and 2 PM and serum YKL-40 increased slightly (47 µg/L vs. 52, 8% difference, P<0.0001).

Figure 7:
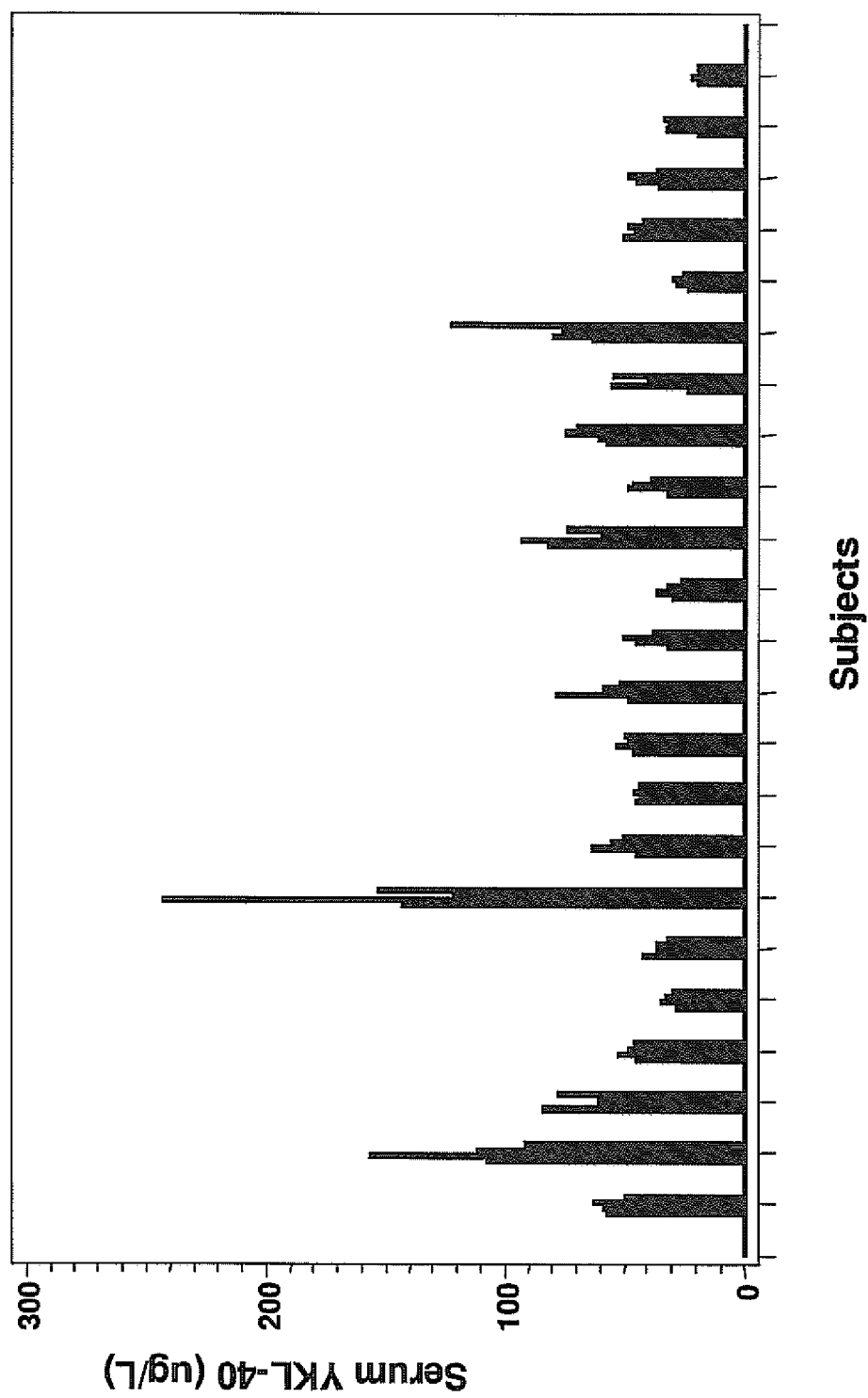
FIG. 7. The median serum YKL-40 level for 23 individuals over 3 weeks available in each of 4 rounds (each bar represents the median of one round for each subject).

FIG. 7 illustrates the individual variation in serum YKL-40 at five time points during a 3 week period (at 8 AM on day 1, 2, 8, 15 and 22, 1st round) and repeated after 6 months (2nd round), 12 months (3rd round) and 24 months (4th round). The median day to day CV of serum YKL-40 for each subject was overall 16% (range 0-92%), and 16% (0-63%, 1st round), 19% (5-92%, 2nd), 15% (0-64%, 3rd), and 21% (0-47%, 4th).

No systematic increases or decreases were detected over the 4 rounds (P=0.09). The estimates of the variance components using a random effects model with serum YKL-40 log transformed results in a within subject CV of 27.3% and a CV over 24 months of 8.8%. The within subject CV including the variation over time and inter-assay variation was 30.2% over the 24 months period. The intraclass correlation coefficient over the 24 months was 72.4%. The estimated variation in serum YKL-40 within subjects including inter-assay variation results in 95% confidence limits for the difference between two measurements on the same subject if the second YKL-40 measurement is reduced by 52% or is increased by 109% and differences of this magnitude are significant and not only a reflection of pre-analytical conditions, methodological and normal biologic variability.

Figure 8:
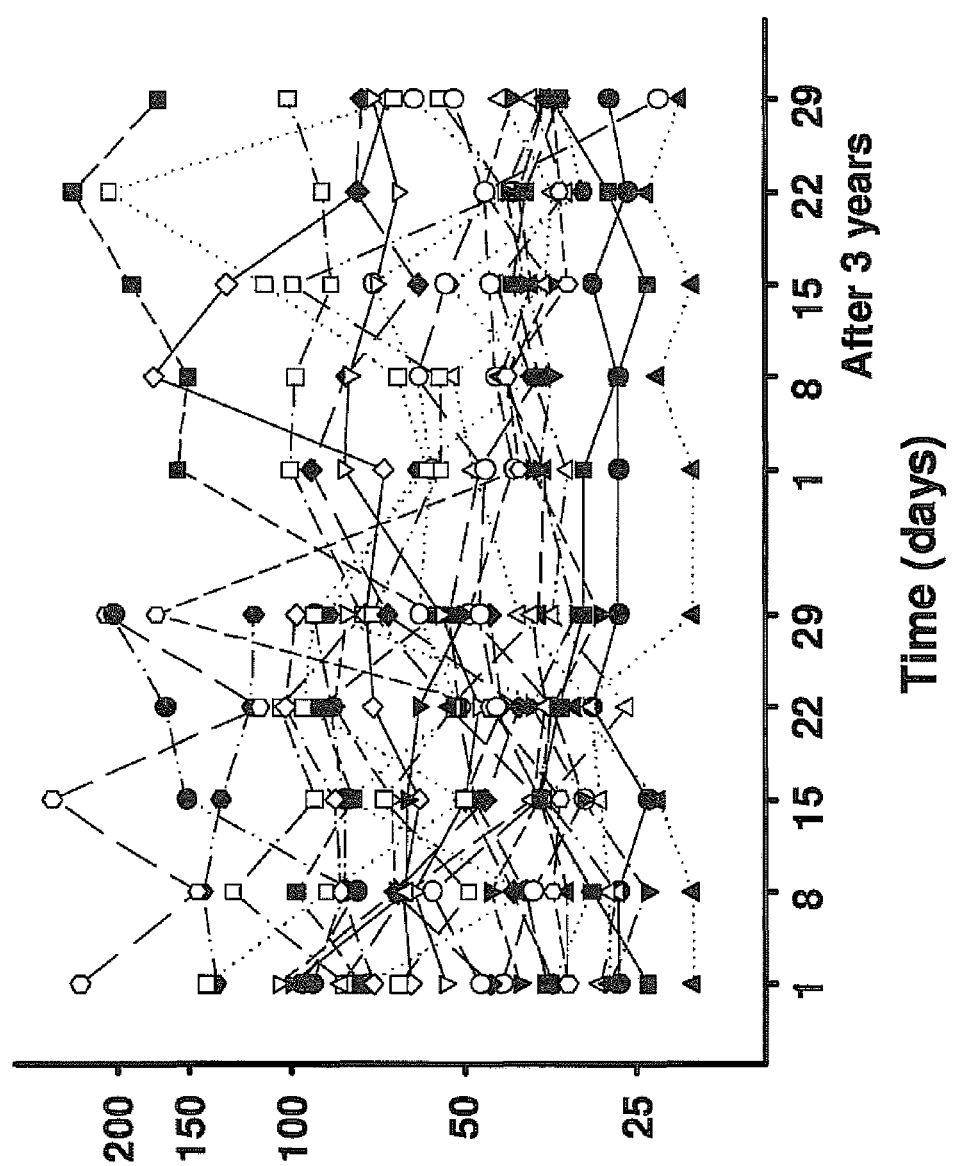
FIG. 8. Individual serum YKL-40 levels of 30 healthy women sampled over 4 weeks and repeated 3 years later for 21 of the women.

FIG. 8 shows the individual weekly changes in serum YKL-40 at five time points during a month and subsequently again after 3 years. The median CV in serum YKL-40 was 17% (1st round) and 13% (2nd round). In subjects analyzed in both rounds (n=21) no changes in serum YKL-40 were observed between the two periods (P=0.37, linear model). The estimates of the variance components using the random effects model with serum YKL-40 log transformed result in a within subject CV of 26.0% and CV over 3 years of 7.3%. The within subject CV including the variation over time and inter-assay variation was 28.8%. The between subject variation including within subject variation and variation over time was 54%. The intraclass correlation coefficient over 3 years was 72.2% suggesting a relatively low within subject variation compared to between subject variation.

CONCLUSIONS

The present study demonstrates that serum YKL-40 is stable in healthy subjects for short term as well as long term sampling periods of up to 3 years with a within subject CV of ~30% including inter-assay variation. The between subject variation in serum YKL-40 was 45% in the study determining a normal reference interval and similar to that found in the other studies of healthy subjects in the present study.

The intraclass correlations of serum YKL-40 were 72.4% and 72.2% over a period of 2 and 3 years, suggesting a relative low within subject variation compared to between subject variations. The intraclass correlations found in the present study are similar to those found for other serological markers, for example Ockene et al. reported an intraclass correlation of 66% for high sensitive C-reactive-protein (Ockene et al., 2001).

The present estimated variation in serum YKL-40 within healthy subjects including inter-assay variation determined that an increase of >109% or a decrease of >52% in serum YKL-40 is considered as significant and not only a reflection of pre-analytical conditions, methodological and normal biologic variability.

In conclusion, the present study showed that there are no significant diurnal variation in serum YKL-40 nor an effect of physical exercise. A relatively low within subject variation compared to between subject variation in serum YKL-40 was demonstrated confirming that that YKL-40 is a reliable biomarker.

REFERENCES

Bigg H F, Wait R, Rowan A D, Cawston T E. The mammalian chitinase-like lectin, YKL-40, binds specifically to type I collagen fibril formation. J Biol Chem 2006; 281:21082-95.

Bojesen S E, Tybjærg-Hansen A, Nordestgaard B G. Integrin β3 leu33pro homozygosity and risk of cancer. J Natl Cancer Inst 2003; 95:1150-7.

Boot R G, van Achterberg T A E, van Aken B E, Renkema G H, Jacobs M J H M, Aerts J M F G, et al. Strong induction of members of the chitinase family of proteins in atherosclerosis. Chitotriosidase and human cartilage gp-39 expressed in lesion macrophages. Arterioscler Thromb Vasc Biol 1999; 19:687-94.

Bunn, et al., U.S. Pat. No. 5,213,961

Clarke R, Shipley M, Lewington S, et al. Underestimation of risk associations due to regression dilution in long-term follow-up of prospective studies. Am J Epidemiol 1999; 150:341-53.

Coligan, et al., Unit 9, Current Protocols in Immunology, Wiley Interscience, 1991).

De Ceuninck F, Gaufillier S, Bonnaud A, Sabatini M, Lesur, C, Pastoureau P. YKL-40 (Cartilage gp-39) induces proliferative events in cultured chondrocytes and synoviocytes and increases glycosaminoglycan synthesis in chondrocytes. Biochem Biophys Res Commun 2001; 285:926-31.

Harlow and Lane, Antibodies, A Laboratory Manual, Cold Spring Harbor Laboratory, 1988.

Harvey S, Weisman M, O'Dell J, et al. Chondrex: new marker of joint disease. Clin Chem 1998; 44:509-16.

Innis, et al., PCR Protocols: A Guide to Methods and Applications, Acad. Press, 1990.

Johansen J S, Williamson M K, Rice J S, Price P A. Identification of proteins secreted by human osteoblastic cells in culture. J Bone Miner Res 1992; 7:501-12.

Johansen J S, Jensen B V, Roslind A, Nielsen D, Price P A. Serum YKL-40, a new prognostic biomarker in cancer patients? Cancer Epidemiol Biomarkers Prey 2006; 15:194-202. A Johansen J S. Studies on serum YKL-40 as a biomarker in diseases with inflammation, tissue remodelling, fibrosis and cancer. Dan Med Bull 2006; 53:172-209. B Juel K, Helweg-Larsen K. The Danish registers of causes of death. Dan Med Bull 1999; 46:354-7.

Kirkwood T B L. Geometric means and measures of dispersion. Biometrics 1979; 35:908-9.

Kohler and Milstein, Nature, 256:495, 1975.

Kohsaka, et al., Nuc. Acids Res., 21:3469-3472, 1993

Kushner I, Rzewnicki D, Samols D. What does minor elevation of C-reactive protein signify? Am J Med 2006; 119: 166.e17-166.e28.

Langone, et al. eds. Acad. Press, 1981.

Ling H, Recklies A D. The chitinase 3-like protein human cartilage glycoprotein 39 inhibits cellular responses to the inflammatory cytokines interleukin-1 and tumour necrosis factor-alpha. Biochem J 2004; 380:651-9.

Millis A J T, Hoyle M, Kent L. In vitro expression of a 38,000 dalton heparin-binding glycoprotein by morphologically differentiated smooth muscle cells. J Cell Physiol 1986; 127:366-72.

Nishikawa K C, Millis A J T. gp38k (CHI3L1) is a novel adhesion and migration factor for vascular cells. Exp Cell Res 2003; 287:79-87.

Nordestgaard B G, Benn M, Schnohr P, Tybjærg-Hansen A. Nonfasting trigycerides and risk of myocardial infarction, ischemic heart disease, and death in men and women. JAMA 2007; 298:299-308.

Ockene I S, Matthews C E, Rifai N, Ridker P M, Reed G, Stanek E. Variability and classification accuracy of serial high-sensitivity C-reactive protein measurements in healthy adults. Clin Chem 2001; 47:444-50.

Recklies A D, White C, Ling H. The chitinase 3-like protein human cartilage 39 (HC-gp39) stimulates proliferation of human connective-tissue cells and activates both extracellular signal-regulated kinase- and protein kinase B-mediated signalling pathways. Biochem J 2002; 365:119-26

Recklies A D, Ling H, White C, Bernier S M. Inflammatory cytokines induce production of CHI3L1 by articular chondrocytes. J Biol Chem. 2005; 280:41213-21.

Remington's Pharmaceutical Sciences, 16th Ed., Mack Publishing Co., Easton, Pa., 1980.

Renkema G H, Boot R G, Au F L, et al. Chitotriosidase, a chitinase, and the 39-kDa human cartilage glycoprotein, a chitin-binding lectin, are homologues of family 18 glycosyl hydrolases secreted by human macrophages. Eur J Biochem 1998; 251:504-9.

Salacinski, et al., Anal. Biochem., 117:136-146, 1981

Schnohr P, Jensen J S, Scharling H, Nordestgaard B G. Coronary heart disease risk factors ranked by importance for the individual and community. A 21 year follow-up of 12 000 men and women from The Copenhagen City Heart Study. Eur Heart J 2002; 23:620-6.

Shackelton L M, Mann D M, Millis A J T. Identification of a 38-kDa heparin-binding glycoprotein (gp38k) in differentiating vascular smooth muscle cells as a member of a group of proteins associated with tissue remodelling. J Biol Chem 1995; 270:13076-83.

The invention claimed is:

1. A method for identifying the presence of an undiagnosed disease or disorder in a subject, said method comprising:
   i) determining the level of YKL-40 in a sample obtained from the subject; and
   ii) comparing said level of YKL-40 with a reference level of YKL-40 selected from the following set of age dependent cut-off values defined as:
   the 90th percentile: natural log(ln)(plasma YKL-40 µg/l) =3.5+0.02×age (years),
   the 95th percentile: ln(plasma YKL-40 µg/l)=3.6+0.02× age (years), and
   the 97.5th percentile: ln(plasma YKL-40 µg/l)=3.9+0.02× age (years),
   wherein the lower the percentile, the higher the sensitivity of the identification, and wherein a level of YKL-40 in the sample above one of said reference levels indicates the presence of the undiagnosed disease or disorder in the subject, thereby identifying the presence of the undiagnosed disease or disorder in the subject.

2. The method according to claim 1, wherein the disease or disorder is one or more diseases or disorders or a group of diseases or disorders that do not provide an elevated C-reactive protein level.

3. The method according to claim 1, wherein the level of one or more additional biomarkers is determined in the same sample as the YKL-40 level.

4. The method according to claim 3, wherein the one or more additional biomarkers are selected from the group consisting of C-reactive protein, ESR, carcinoembryonic antigen (CEA), CA-125, human epidermal growth factor receptor 2 (HER2), CA19-9, lactate dehydrogenase (LDH), tissue inhibitor metalloproteinase I (TIMP-1), brain natriuretic protein, interleukins, tumor necrosis factor-alpha, homocysteine, amyloid A protein, pregnancy-associated plasma protein-A, troponins, soluble intercellular adhesion molecule-1, soluble UPAR, the amino-terminal propeptide of type III procollagen (P-III-NP), monocyte chemoattractant protein 1, fibrin D-dimer, growth-differentiation factor-15, ischemia-modified albumin, lipoprotein-associated phospholipase A2, matrix metalloproteinases, and CKMB.

5. The method according to claim 1, wherein the biological sample is blood, serum, or plasma.

6. The method of claim 1, wherein the YKL-40 age dependent reference level is defined as the 90th percentile: ln(plasma YKL-40 µg/l)=3.5+0.02×age (years).

7. The method of claim 1, wherein the YKL-40 age dependent reference level is defined as the 95th percentile: ln(plasma YKL-40 µg/l)=3.6+0.02×age (years).

8. The method of claim 1, wherein the YKL-40 age dependent reference level is defined as the 97.5th percentile: ln(plasma YKL-40 µg/l)=3.9+0.02×age (years).

9. The method of claim 1, wherein the undiagnosed disease or disorder is a yet unknown disease or disorder.

10. A method for identifying the presence of an undiagnosed a disease or disorder in a subject, said method comprising
    i) determining the level of YKL-40 in a sample obtained from the subject; and
    ii) comparing said level of YKL-40 with an age adjusted reference level of YKL-40, said reference level being a previously determined level of YKL-40 from the same subject;
    wherein an increase of at least a factor of 1.60 in the level of YKL-40 in the sample compared to the reference level of YKL-40 indicates the presence of the undiagnosed disease or disorder in the subject, thereby identifying the presence of the undiagnosed disease or disorder in the subject.

11. The method according to claim 10, wherein said reference level is age adjusted by adding 0.5 µg/l per year for women and 0.8 µg/l per year for men.

12. The method according to claim 10, wherein said level of YKL-40 in the sample is said to be significantly above the reference level and thereby indicating the presence of the undiagnosed disease or disorder when the level of YKL-40 in the sample is increased by about 109% or more.

13. The method according to claim 10, wherein a level of YKL-40 in the sample being increased to at least a factor of 1.70, 1.75, 1.80, 1.90, 2, 2.10, 2.20, 2.25, or 2.50 compared to the YKL-40 reference level indicates the presence of the undiagnosed disease or disorder.

14. A method for classifying the severity of an undiagnosed disease or disorder in a subject, said method comprising
    i) determining the level of YKL-40 in a sample obtained from the subject; and
    ii) comparing the level of YKL-40 with one or more reference levels of YKL-40 from the following set of age adjusted cut-off values defined as:
    the 90th percentile: ln(plasma YKL-40 µg/l)=3.5+0.02× age (years), the 95th percentile: ln(plasma YKL-40 µg/l)=3.6+0.02× age (years), and the 97.5th percentile: ln(plasma YKL-40 µg/l)=3.9+0.02× age (years);

wherein the higher the percentile, the more severe the classification for the undiagnosed disease or disorder, or comparing the level of YKL-40 with one or more previously determined age adjusted_levels of YKL-40 from the same subject, wherein a level of YKL-40 in the sample being increased to at least a factor of 1.60 or more compared to the one or more previously determined age adjusted levels of YKL-40 indicates that the undiagnosed or disorder has evolved to a more severe stage of the disease or disorder, or wherein a level of YKL-40 in the sample being decreased at least to a factor of 0.60 compared to the one or more previously determined age adjusted levels of YKL-40 indicates that the undiagnosed disease or disorder has evolved to a less severe stage of the disease or disorder; wherein the severity of said undiagnosed disease or disorder is deduced from said comparison.

15. The method according to claim 14, wherein the one or more previously determined age adjusted levels of YKL-40 from the same subject are age adjusted by adding 0.5 µg/l per year for women and 0.8 µg/l per year for men.

16. The method according to claim 14, wherein a level of YKL-40 in the sample being increased to at least a factor of 1.70, 1.75, 1.80, 1.90, 2, 2.10, 2.20, 2.25, or 2.50 compared to the one or more previously determined age adjusted levels of YKL-40 from the same subject indicates that the undiagnosed disease or disorder has evolved to a more severe stage of the disease or disorder.

17. The method according to claim 14, wherein a level of YKL-40 in the sample being decreased at least to a factor of 0.50, 0.48, 0.45, 0.43, 0.40, or 0.38 compared to the one or more previously determined age adjusted levels of YKL-40 from the same subject indicates that the undiagnosed disease or disorder has evolved to a less severe stage of the disease or disorder.

18. The method according to claim 14, wherein a level of YKL-40 in the sample being increased by 109% compared to the one or more previously determined age adjusted levels of YKL-40 indicates that the undiagnosed disease or disorder has evolved to a more severe stage of the disease or disorder.

19. The method according to claim 14, wherein a level of YKL-40 in the sample being decreased by 52% compared to the one or more previously determined age adjusted levels of YKL-40 indicates that the undiagnosed disease or disorder has evolved to a less severe stage of the disease or disorder.

20. The method according to claim 14, wherein the determined level of YKL-40 in the sample above one or more of the reference levels provides the classification of the undiagnosed disease or disorder.

21. The method according to claim 14, wherein the classification of the undiagnosed disease or disorder is provided by comparing the determined YKL-40 level from the sample with the one or more reference levels of YKL-40, wherein the higher the level of YKL-40 the more severe the classification for the undiagnosed disease or disorder.

* * * * *